United States Patent
Erdem et al.

(10) Patent No.: US 11,285,056 B2
(45) Date of Patent: *Mar. 29, 2022

(54) TOPSHEET COMPRISING NATURAL FIBERS WITH GOOD MECHANICAL STRENGTH

(71) Applicant: The Procter & Gamble Company, Cincinnati, OH (US)

(72) Inventors: Gueltekin Erdem, Beijing (CN); Rodrigo Rosati, Frankfurt am Main (DE)

(73) Assignee: The Procter & Gamble Company, Cincinnati, OH (US)

(*) Notice: Subject to any disclaimer, the term of this patent is extended or adjusted under 35 U.S.C. 154(b) by 385 days.

This patent is subject to a terminal disclaimer.

(21) Appl. No.: 16/382,273

(22) Filed: Apr. 12, 2019

(65) Prior Publication Data

US 2019/0231612 A1 Aug. 1, 2019

Related U.S. Application Data

(63) Continuation of application No. PCT/CN2018/110397, filed on Oct. 16, 2018, and a continuation-in-part of application No. PCT/CN2017/106835, filed on Oct. 19, 2017.

(51) Int. Cl.
*A61F 13/15* (2006.01)
*A61F 13/513* (2006.01)
(Continued)

(52) U.S. Cl.
CPC ...... *A61F 13/513* (2013.01); *A61F 13/15699* (2013.01); *A61F 13/49413* (2013.01);
(Continued)

(58) Field of Classification Search
CPC .............. A61F 13/513; A61F 13/15699; A61F 13/49413; A61F 13/51104;
(Continued)

(56) References Cited

U.S. PATENT DOCUMENTS

| 4,324,247 A | 4/1982 | Aziz |
| 4,629,643 A | 12/1986 | Curro |

(Continued)

FOREIGN PATENT DOCUMENTS

| CN | 2430146 | 5/2001 |
| CN | 1682675 A | 10/2005 |

(Continued)

OTHER PUBLICATIONS

International Search Report and Written Opinion; Application Ser. No. PCT/CN2018/110397; dated Feb. 3, 2019, 9 pages.
(Continued)

*Primary Examiner* — Jacqueline F Stephens
(74) *Attorney, Agent, or Firm* — Christian M. Best

(57) ABSTRACT

A topsheet for use with an absorbent article is provided and comprises a first layer and a second layer. The first layer is a spunlace nonwoven and comprises at least 15% by weight of natural fibers by total weight of the first layer. The first layer comprises a plurality of protrusions and a plurality of apertures. The first layer and the second layer are in contact with each other between the plurality of the protrusions. The second layer has a plurality of apertures at least partially aligned with the apertures of the first layer. The first layer has a minimum CD strength of at least 3N/(5 cm), according to the Tensile Strength Test Method.

20 Claims, 15 Drawing Sheets

(51) Int. Cl.

| | | |
|---|---|---|
| *A61F 13/511* | (2006.01) | |
| *A61F 13/512* | (2006.01) | |
| *A61F 13/537* | (2006.01) | |
| *A61F 13/494* | (2006.01) | |
| *A61L 15/40* | (2006.01) | |
| *A61L 15/42* | (2006.01) | |
| *A61F 13/51* | (2006.01) | |
| *A61F 13/539* | (2006.01) | |
| *B32B 3/30* | (2006.01) | |
| *B32B 5/02* | (2006.01) | |

(52) U.S. Cl.
CPC ........ *A61F 13/512* (2013.01); *A61F 13/5116* (2013.01); *A61F 13/5125* (2013.01); *A61F 13/51104* (2013.01); *A61F 13/51121* (2013.01); *A61F 13/53752* (2013.01); *A61L 15/40* (2013.01); *A61L 15/42* (2013.01); *A61F 2013/15292* (2013.01); *A61F 2013/15447* (2013.01); *A61F 2013/51007* (2013.01); *A61F 2013/51019* (2013.01); *A61F 2013/51165* (2013.01); *A61F 2013/53908* (2013.01); *B32B 3/30* (2013.01); *B32B 5/022* (2013.01); *B32B 2262/0284* (2013.01); *B32B 2262/062* (2013.01); *B32B 2307/726* (2013.01)

(58) Field of Classification Search
CPC ............ A61F 13/51121; A61F 13/5116; A61F 13/512; A61F 13/5125; A61F 13/53752; A61F 2013/15292; A61F 2013/15447; A61F 2013/51007; A61F 2013/51019; A61F 2013/51165; A61F 2013/53908; B32B 3/30; B32B 5/022; B32B 2262/0284; B32B 2262/062; B32B 2307/726

See application file for complete search history.

(56) References Cited

U.S. PATENT DOCUMENTS

| | | | |
|---|---|---|---|
| 4,804,378 | A | 2/1989 | Shiba et al. |
| 5,273,596 | A | 12/1993 | Newkirk |
| 5,628,097 | A | 5/1997 | Benson |
| 5,656,232 | A | 8/1997 | Takai et al. |
| 5,658,639 | A | 8/1997 | Curro et al. |
| 6,320,096 | B1 | 11/2001 | Inoue et al. |
| 6,702,917 | B1 | 3/2004 | Venturino et al. |
| 2002/0064639 | A1 | 5/2002 | Rearick et al. |
| 2003/0113548 | A1 | 6/2003 | Corzani et al. |
| 2004/0127875 | A1* | 7/2004 | Hammons ......... A61F 13/51104 604/385.01 |
| 2004/0265534 | A1* | 12/2004 | Curro ....................... B32B 5/18 428/92 |
| 2005/0054999 | A1 | 3/2005 | Morman et al. |
| 2005/0154362 | A1 | 7/2005 | Warren et al. |
| 2006/0286343 | A1 | 12/2006 | Curro |
| 2008/0221538 | A1 | 9/2008 | Zhao |
| 2011/0302733 | A1 | 12/2011 | Yuan |
| 2012/0321839 | A1 | 12/2012 | Uematsu et al. |
| 2014/0121625 | A1 | 5/2014 | Kirby et al. |
| 2014/0234575 | A1 | 8/2014 | Mitsuno |
| 2014/0276512 | A1 | 9/2014 | Cheng et al. |
| 2014/0336608 | A1 | 11/2014 | Hao et al. |
| 2015/0038934 | A1 | 2/2015 | Day et al. |
| 2015/0250662 | A1 | 9/2015 | Isele et al. |
| 2015/0283001 | A1 | 10/2015 | Arizti et al. |
| 2016/0074251 | A1 | 3/2016 | Strube et al. |
| 2016/0074255 | A1 | 3/2016 | Strube et al. |
| 2016/0076184 | A1 | 3/2016 | Orr et al. |
| 2016/0153128 | A1 | 6/2016 | Xie et al. |
| 2017/0258646 | A1 | 9/2017 | Grenier et al. |
| 2017/0259550 | A1 | 9/2017 | Neton et al. |
| 2017/0348167 | A1 | 12/2017 | Tashiro et al. |
| 2018/0051404 | A1 | 2/2018 | Novarino et al. |
| 2018/0177646 | A1 | 6/2018 | Burger et al. |
| 2019/0053958 | A1 | 2/2019 | Kurihara et al. |
| 2019/0117472 | A1 | 4/2019 | Erdem et al. |
| 2019/0117473 | A1 | 4/2019 | Rosati et al. |
| 2019/0240084 | A1 | 8/2019 | Rosati et al. |
| 2020/0179177 | A1 | 6/2020 | Erdem et al. |

FOREIGN PATENT DOCUMENTS

| | | |
|---|---|---|
| CN | 101443499 A | 5/2009 |
| CN | 101892557 A | 11/2010 |
| CN | 1839776 | 4/2011 |
| CN | 102673030 A | 9/2012 |
| CN | 202637294 U | 1/2013 |
| CN | 103156735 A | 6/2013 |
| CN | 101940514 B | 12/2013 |
| CN | 106048888 | 10/2016 |
| CN | 106192268 | 12/2016 |
| JP | 2005324010 A | 11/2005 |
| JP | 2008099947 A | 5/2008 |
| JP | 2010279621 A | 12/2010 |
| JP | 5094992 B2 | 12/2012 |
| JP | 2017153915 A | 9/2017 |
| WO | 0019949 A1 | 4/2000 |
| WO | 2013042501 A1 | 3/2013 |
| WO | 2016040101 A1 | 3/2016 |
| WO | WO2016040096 A1 | 3/2016 |
| WO | 2017033867 A1 | 3/2017 |

OTHER PUBLICATIONS

All Office Actions, U.S. Appl. No. 16/382,259.
All Office Actions, U.S. Appl. No. 16/141,086.
All Office Actions, U.S. Appl. No. 16/141,129.
International Search Report and Written Opinion, PCT/CN2017/106835.

* cited by examiner

TOPSHEET COMPRISING NATURAL FIBERS WITH GOOD MECHANICAL STRENGTH

CROSS REFERENCE TO RELATED APPLICATION

This application is a continuation, and claims priority under 35 U.S.C. § 120, of Patent Application No. PCT/CN2018/110397, filed on Oct. 16, 2018, which is a continuation-in-part to Patent Application No. PCT/CN2017/106835, filed on Oct. 19, 2017, which are hereby incorporated by reference herein in their entirety.

FIELD

The present disclosure provides a three-dimensional topsheet having a good structural and mechanical strength. The topsheet may be used in an absorbent article for personal hygiene such as a baby diaper, a training pant, a feminine hygiene sanitary napkin or an adult incontinence product.

BACKGROUND

Absorbent articles for personal hygiene, such as disposable diapers for infants, training pants for toddlers, adult incontinence undergarments and/or sanitary napkins are designed to absorb and contain body exudates, in particular large quantities of urine, runny bowel movement (BM) and/or menses. These absorbent articles may comprise several layers providing different functions, for example, a topsheet, a backsheet, and an absorbent core disposed between the topsheet and the backsheet, among other layers (e.g. acquisition layer, distribution layer, etc.) if desired.

The topsheet is generally liquid permeable and is configured to receive the fluids being excreted from the body and aid in directing the fluids toward an acquisition system, a distribution system, and/or the absorbent core. In general, topsheets may be made to be hydrophilic via a surfactant treatment applied thereto so that the fluids are attracted to the topsheet to then be channeled into the underlying acquisition system, distribution system, and/or absorbent core. One of the important qualities of a topsheet is the ability to reduce ponding of the fluids on the topsheet before the fluids are able to be absorbed by the absorbent article.

Three-dimensional topsheet have been developed; see for example U.S. Patent application US2014/0121625 A1. Such three-dimensional topsheet may also be apertured. Three-dimensional apertured topsheet may be created via patterning processes such as hot male/female embossing or hot pin processes. These three-dimensional topsheets have good fluid handling properties.

The topsheet may comprise natural fibers, such as cotton or bamboo fibers which are natural cellulose fibers known to have characteristics of being soft, biodegradable and less likely to cause allergies, irritations or rashes.

The present disclosure provides a topsheet comprising natural fibers for use in an absorbent article that has improved structural and mechanical strength.

SUMMARY

A topsheet for use with an absorbent article is disclosed, the topsheet comprising a first layer and a second layer. The second layer is in a face to face relationship with the first layer. The first layer is a spunlace nonwoven and comprises at least 15% by weight, or at least 30% by weight, or at least 50% by weight, or at least 60% by weight, or at least 75% by weight, or at least 95% by weight of natural fibers by total weight of the first layer. The first layer comprises a plurality of protrusions and a plurality of apertures. The plurality of apertures is located between the majority of the protrusions, and the plurality of protrusions imparts a three-dimensional shape to the first layer. The first layer and the second layer are in contact with each other between the majority of the protrusions. The second layer has a plurality of apertures at least partially, or completely aligned with the apertures of the first layer. The first layer at least partially penetrates the second layer of the topsheet at the apertures.

The first layer has a minimum CD strength of at least 3N/(5 cm), or at least 5N/(5 cm), or at least 8N/(5 cm) according to the tensile strength test method. The first layer may have a CD strength of not more than 25N/(5 cm), or not more than 20N/(5 cm), or not more than 15N/(5 cm).

The inventors have found that having a three-dimensional, apertured topsheet with a first layer having at least 15% by weight, or at least 30% by weight, or at least 50% by weight, or at least 60% by weight, or at least 75% by weight, or at least 95% by weight of natural fiber and a minimum CD strength of at least 3N/(5 cm) provides a topsheet with improved structural and mechanical strength. During the patterning processes, the topsheet as described above is not damaged and does not create fuzz of natural fibers and/or synthetic fibers. The risk of having irritations and rashes on the skin of the wearer of the absorbent article is decreased.

The topsheet may have an Abrasion Integrity Parameter of at least 80 cycles, or of from 80 to 480 cycles, or of from 80 to 400 cycles, or of from 80 to 350 cycles, or of from 100 to 350 cycles, when measured according to the Martindale Abrasion Resistance Test Method set out herein below.

Moreover, the topsheet of the present disclosure comprising a first layer and a second layer having a plurality of apertures allows a better absorption of body fluids. The topsheet can reduce the contact of the liquid bodily exudates with the skin of the wearer. Therefore, the topsheet is sufficiently dry when in contact with the skin of the wearer of the absorbent article.

Furthermore, providing a three-dimensional first layer of the topsheet reduces the skin/body fluids contact and/or the skin/body fluids contact time during a urination event. The skin discomfort for the wearer of the absorbent article is reduced.

Besides, as the first layer of the topsheet may be in direct contact with the skin during use conditions, having a high content of natural fibers, such as cotton fibers, in the first layer of the topsheet enables to have a soft feel for the wearer's skin as well as to increase the amount of biodegradable material in contact with the wearer's skin and to decrease the risk of allergies, irritations or rashes on the skin of the wearer of the absorbent article.

The first layer may be a cross-lapped spunlace nonwoven layer. The fibers of the first layer may be cross-lapped in a CD direction (Cross Direction), transverse to the MD direction (Machine Direction). Therefore, such cross-lapped spunlace nonwoven layer has improved structural and mechanical strength.

The first layer may comprise synthetic fibers (e.g. thermoplastic fibers), such as heat fusible fibers. Such fibers may be mixed with natural fibers in the first layer of the topsheet. The heat fusible fibers may slightly melt during the drying step of the spunlacing process. Thus, the heat fusible fibers may provide additional mechanical strength to the first layer of the topsheet.

Moreover, the heat fusible fibers may enable to bond the first layer and the second layer of the topsheet via embossing.

Alternatively, the first layer may be a nonwoven layer composed of a carrier web and of a web comprising natural fibers, with at least some of the fibers of the web comprising natural fibers interpenetrating with at least some of the fibers of the carrier web.

The carrier web may comprise spunbond fibers or carded fibers.

Since part of the web comprising natural fibers enters the carrier web, the web comprising natural fibers has enhanced mechanical strength such as tensile strength, therefore improving the mechanical strength of the topsheet.

The natural fibers may be selected from the group consisting of cotton fibers, bamboo fibers, or a mixture thereof.

The plurality of apertures may be uniformly distributed on the first layer.

The topsheet may have a run-off of less than 40% according to the run-off test method.

The topsheet as described above also provides improved fluid handling properties such as reduced rewet onto the wearer-facing surface of the absorbent article and better liquid acquisition.

The second layer may include synthetic fibers, natural fibers and/or combinations thereof. The synthetic fibers may be single component fibers, multi-component fibers and combinations thereof.

The second layer may have no protrusions.

Alternatively, the second layer may comprise a plurality of protrusions. The plurality of protrusions may impart a three-dimensional shape to the second layer. The plurality of protrusions of the first layer may be at least partially aligned with the plurality of protrusions of the second layer.

The second layer may have a higher machine direction (MD) strength than the first layer. A second layer having a higher MD strength is able to bear the tension, e.g. when winding or converting the topsheet, thus "protecting" the first layer when the topsheet experiences tension. For example, the MD strength of the second layer may be at least 25% higher, or at least 50% higher, or at least 75% higher, or at least 100% higher than the MD strength of the first layer. The MD strength of the second layer may be from 15 N/5 cm to 100 N/5 cm.

The topsheet forms a three-dimensional laminate of two layers in a face to face relationship. Having a laminate of two layers in a face to face relationship improves the dewatering of the first layer upon contact with liquid bodily exudates. Therefore, when the topsheet comprising a laminate of two layers is incorporated into an absorbent article, this topsheet can reduce the contact of the liquid bodily exudates with the skin of the wearer.

Moreover, it may also reduce rewet onto the wearer-facing surface of the absorbent article.

The present disclosure also relates to an absorbent article comprising a longitudinal centerline, a transversal centerline perpendicular to the longitudinal centerline, a topsheet as described herein, an absorbent core and a backsheet. The absorbent core is positioned intermediate the backsheet and the topsheet. The first layer of the topsheet is in contact with the skin of the wearer during use of the absorbent article and the second layer is facing towards the absorbent core.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Definition of Terms

Figure 1:
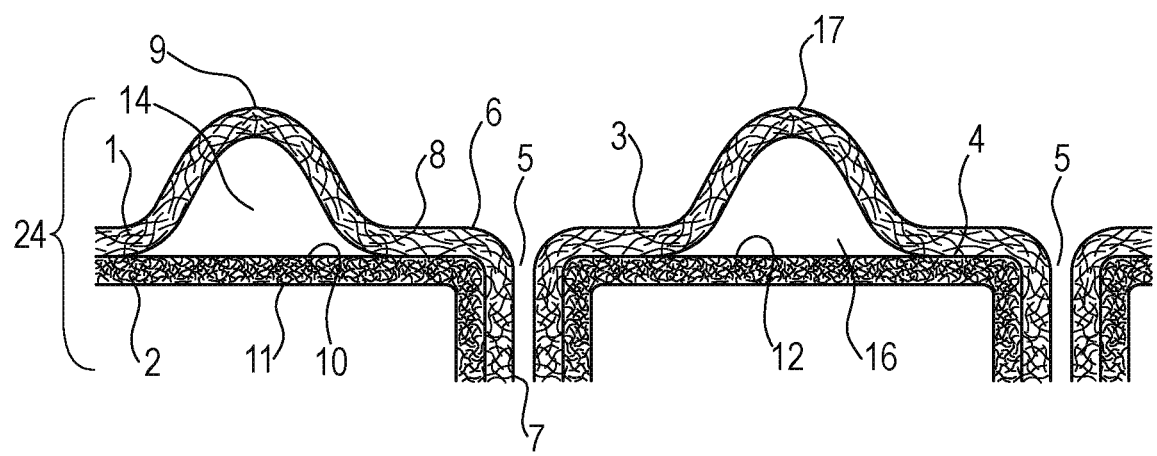
FIG. 1 is a schematic view of a topsheet having a three-dimensional first layer and a second layer free of protrusions in accordance with the present disclosure.

The term "absorbent article" as used herein refers to disposable products such as diapers, pants or feminine hygiene sanitary napkins and the like which are placed against or in proximity to the body of the wearer to absorb and contain the various liquid bodily exudates discharged from the body. Typically, these absorbent articles comprise a topsheet, backsheet, an absorbent core and optionally an acquisition layer and/or distribution layer and other components, with the absorbent core normally placed between the backsheet and the acquisition system or topsheet. The absorbent article of the present disclosure may be a diaper or pant.

The term "diaper" as used herein refers to an absorbent article that is intended to be worn by a wearer about the lower torso to absorb and contain liquid bodily exudates discharged from the body. Diapers may be worn by infants (e.g. babies or toddlers) or adults. They may be provided with fastening elements.

The term "pant" as used herein refers to an absorbent article having fixed edges, a waist opening, and leg openings designed for infant or adult wearers. A pant is placed in position on the wearer by inserting the wearer's legs into the leg openings and sliding the pant-type absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be pre-formed anywhere along the circumference of the article (e.g., side fastened, front waist fastened).

The term "mechanical strength" or "strength" refers to the ability of material to withstand the stress of physical forces. It can correspond to the amount of weight or of longitudinal strength a material can support without being damaged or deformed.

The term "CD strength" refers to a force applied in a Cross Direction during the tensile strength test method (i.e. the CD strength test method with Cross direction (CD) being the opposite of Machine Direction (MD)).

The term "MD strength" refers to a force applied in a Machine Direction during the tensile strength test method (i.e. the MD strength test method with Machine direction being the opposite of Cross Direction).

The term "damage" means a physical harm that impairs the value, the usefulness or the normal function of a material, such as a topsheet of an absorbent article.

The degree of hydrophilicity or hydrophobicity can be measured in each case by determining the contact angle of water with the specific material.

The term "hydrophilic" refers to a material having a contact angle of less than or equal to 70° according to the contact angle test method described herein.

The term "hydrophobic" refers to a material having a contact angle greater than 70° according to the contact angle test method described herein.

The term "a majority of the apertures" as used herein means that more than 50%, or more than 60%, or more than 70%, or more than 80%, or more than 90%, up to 100% of the apertures in the topsheet.

The term "bonding areas" means the areas where the first layer and the second layer of the topsheet of the present disclosure are joined together or are attached to each other through several methods of bonding to form a topsheet.

The term "web" as used herein means a material capable of being wound into a roll. Webs may be nonwovens.

The term "nonwoven web" as used herein refers to a manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

The term "spunlace nonwoven" means a nonwoven wherein the cohesion and the interlacing of the fibers with one another is obtained by means of a plurality of jets of water under pressure passing through a moving fleece or cloth and, like needles, causing the fibers to intermingle with one another. These spunlace nonwovens are essentially defined by the fact that their consolidation results from hydraulic interlacing. "Spunlace nonwoven", as used herein, also relates to a nonwoven formed of two webs, which are combined with each other by hydraulic interlacing. The two webs, prior to being combined into one nonwoven by hydraulic interlacing, may have underdone bonding processes, such as heat and/or pressure bonding by using e.g. a patterned calendar roll and an anvil roll to impart a bonding pattern. However, the two webs are combined with each other solely by hydraulic interlacing.

The term "cellulosic fiber" as used herein refers to natural fibers which typically are wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web.

The term "heat fusible fibers" means fibers that when they are heated at a certain temperature, the fibers can fusion bond to other fibers that comprise the same material or different material from the heat fusible fibers.

The Topsheet Comprising Natural Fibers:

Nonwoven webs comprising substantial amounts of natural fibers cannot be consolidated via heat fusion or thermal bonding. Hence, such nonwoven webs comprising natural fibers are often consolidated into a coherent, stable web by using spunlacing processes with water jets. Such nonwoven webs are referred to as spunlace nonwoven webs.

Nonwoven webs comprising natural fibers may be textured, via patterning process for example, to form three-dimensional topsheet with specific aesthetics properties and/or functionality properties.

However, while patterning processes such as hot female/male embossing or hot pin processes exist to create three-dimensional, apertured topsheet, these processes have limited application to nonwoven webs comprising natural fibers. Indeed, it is very difficult to impart a durable three-dimensional structure to a web comprising substantial amounts of natural fibers. Thus, when nonwoven webs comprising natural fibers are modified with such processes, the resultant web cannot be easily stabilized.

Therefore, for the present disclosure, a topsheet is provided which comprises a first and a second layer, wherein the first layer is a spunlace nonwoven comprising natural fibers. The second layer may comprise thermoplastic fibers. The first and second layer are joined to each other, such as by using adhesive, and thereby, the second layer facilitates stabilization of the three-dimensional configuration of the first layer, which has been imparted in the first layer prior to joining it with the second layer.

Moreover, during the patterning processes, there is a high risk of damaging the first layer comprising natural fibers by reducing its strength or by having a high fuzz level creating in-use integrity problems. The fuzz level corresponds to the amount of untangled fibers which protrude from the surface of the topsheet. Having a high fuzz level increases the feeling of skin irritation as well as the skin itchiness for the wearer of the absorbent article.

The risk of damaging during the patterning process is due to the straining which is required in the first layer in order to impart the protrusions. Synthetic fibers, such as thermoplastic fibers typically are relatively long or essentially endless (e.g. in spunbond nonwoven webs), or they are cut to a defined length (so-called staple fibers). While man-made staple fibers have a certain fiber length with a very narrow distribution (e.g. 38 mm+/−3 mm), natural fibers, such as cotton fibers, have a relatively wide distribution of fiber length. In a spunlace material the fibers are held together by entanglement and fiber/fiber friction. Therefore, the fraction of short fibers in cotton fibers, creates difficulties to achieve good mechanical strength and fuzz resistance. This becomes even more difficult when such nonwoven is further processed to create apertures and a three-dimensional structure (e.g. by imparting protrusions) due to the additional mechanical stress and strain the material needs to go through.

Natural fibers, such as cotton fibers may have a fiber length distribution of from 8 mm to 30 mm. Examples for fiber length distribution of commercially available cotton fibers are given below. Due to the number of fibers of relatively short length among the fibers, the risk that these short fibers are drawn out of the spunlace layer (fuzzing) during straining and local elongation of the layer while imparting the protrusions is increased versus layers having synthetic fibers. Also, in use conditions when the natural fibers are in contact with the skin of the wearer, the risk of fuzzing of natural fibers is increased versus synthetic fibers due to friction between the skin and the layer, as the shorter fibers are more prone to fuzzing. The attachment of the first layer to a second layer can help to immobilize the shorter fibers in the first layer, thus reducing the risk of rubbing.

Furthermore, natural fibers are highly hydrophilic. While hydrophilicity facilitates absorption and penetration of body liquids through the topsheet, such topsheets stay typically rather wet due to residual liquid remaining in the topsheet and liquid passing back into (and through) the topsheet from components underneath the topsheet. Therefore, a topsheet comprising natural fibers may be treated with a hydrophobic treatment in order to improve the dryness of the topsheet. In this case, the spunlace nonwoven used in the topsheet may lose strength because the hydrophobic treatment may reduce the fiber to fiber friction within the nonwoven.

The topsheet of the present disclosure is the part of the absorbent article that is in contact with the wearer's skin during use of the article. The topsheet may be joined to portions of the backsheet, the absorbent core, the barrier leg cuffs of an absorbent article, and/or any other layers as is known to those of ordinary skill in the art. Further, at least a portion of, or all of, the topsheet may be liquid permeable, permitting liquid bodily exudates to readily penetrate through its thickness.

The topsheet of the present disclosure comprises natural fibers and may further comprise synthetic fibers.

Synthetic fibers may be selected from the group consisting of polyesters, polypropylenes, polyethylenes, poly ethers, polyamides, polyhydroxyalkanoates, polysaccharides, and combinations thereof. More specifically, Synthetic fibers may be selected from the group consisting of polyethylene terephthalate, polybutylene terephthalate, poly(1, 4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer, polycaprolactone, polyhydroxyl ether ester, polyhydroxyl ether amide, polyesteramide, polylactic acid, polyhydroxybutyrate, and combinations thereof. Additionally, other synthetic fibers such as rayon, polyethylene, and polypropylene fibers can be used within the scope of the present disclosure.

The synthetic fibers may be polypropylene, polyethylene, polyester, polyethylene terephthalate, polybutylene terephthalate, polyamide, polylactic acid, and combinations thereof.

Further, the synthetic fibers may be single component fibers (i.e., single synthetic material or a mixture to make up the entire fiber), multicomponent fibers, such as bicomponent fibers (i.e., the fiber is divided into regions, the regions including two or more different synthetic materials or mixtures thereof), and combinations thereof.

Nonlimiting examples of suitable bicomponent fibers are fibers made of copolymers of polyester (polyethylene terephthalate/isophtalate/polyester (polyethylene terephthalate) otherwise known as "CoPET/PET" fibers, which are commercially available from Fiber Innovation
Technology, Inc., Johnson City, Tenn.

The topsheet may also comprise semi-synthetic fibers made from polymers, specifically hydroxyl polymers. Nonlimiting examples of suitable hydroxyl polymers include polyvinyl alcohol, starch, starch derivatives, chitosan, chitosan derivatives, cellulose derivatives such as viscose, gums, arabinans, galactans, Lyocell (Tencel®) and combinations thereof.

Natural fibers may be selected from the group consisting of wheat straw fibers, rice straw fibers, flax fibers, bamboo fibers, cotton fibers, jute fibers, hemp fibers, sisal fibers, bagasse fibers, hesperaloe fibers, miscanthus, marine or fresh water algae/seaweeds and combinations thereof.

The natural fibers may be selected from the group consisting of cotton fibers, bamboo fibers, or mixtures thereof.

One suitable nonwoven material as a topsheet may be an extensible polypropylene/polyethylene spunbonded nonwoven. One suitable nonwoven material as topsheet may be a spunbonded nonwoven comprising polypropylene and polyethylene. The fibers may comprise a blend of polypropylene and polyethylene. Alternatively, the fibers may comprise bicomponent fibers, such as a sheath-core fiber with polyethylene on the sheath and polypropylene in the core of the fiber.

The topsheet may have a basis weight from 8 to 80 $g/m^2$, or from 8 to 60 $g/m^2$, or from 8 to 50 $g/m^2$, or from 10 to 40 $g/m^2$.

The topsheet of the present disclosure comprises a first layer and a second layer. The second layer is in face to face relationship with the first layer. The first layer of the topsheet may be in direct contact with the wearer's skin. The first layer may have a basis weight of from 10 $g/m^2$ to 50 $g/m^2$, or from 15 $g/m^2$ to 40 $g/m^2$. The second layer may have a basis weight of from 5 $g/m^2$ to 50 $g/m^2$, or from 7 $g/m^2$ to 30 $g/m^2$, or from 7 $g/m^2$ to 20 $g/m^2$. The second layer may have a basis weight that is at least 5 $g/m^2$ lower, or at least 10 $g/m^2$ lower than the basis weight of the first layer. It has been found that such relatively low basis weight layers are sufficient to facilitate stabilization of the three-dimensional configuration of the first layer.

The topsheet may be formed of two layers or, of multiple layers.

Three-Dimensional First Layer:

The first layer is a spunlace nonwoven.

The first layer comprises natural fibers and may further comprise synthetic fibers. The list of synthetic fibers and of natural fibers corresponds to the list disclosed above for the topsheet.

The nonwoven web can be formed from many processes, such as, for example, air laying processes, wetlaid processes, meltblowing processes, spunbonding processes, needle punching processes and carding processes. The fibers in the nonwoven web can then be bonded via spunlacing processes (hydroentangling processes) with water jets.

The synthetic fibers may be polypropylene, polyethylene, polyester, polyethylene terephthalate, polybutylene terephthalate, polyamide, polylactic acid, and combinations thereof.

The natural fibers may be cotton fibers, bamboo fibers, or mixtures thereof.

Cotton fibers are natural cellulosic fibers that have good liquid acquisition, good breathability and good softness. Therefore, having a topsheet comprising a first layer of cotton fibers improves the softness of the topsheet while improving the fluid handling properties of the topsheet.

The first layer may comprise heat fusible fibers, which may be mixed with natural fibers in the first layer of the topsheet.

The first layer comprises at least 15% by weight, or at least 30% by weight, or at least 50% by weight, or at least 60% by weight, or at least 75% by weight, or at least 95% by weight of natural fibers, such as cotton fibers, by total weight of the first layer. The first layer may also be made of 99% to 100% by weight of natural fibers, such as cotton fibers, by total weight of the first layer.

As the first layer of the topsheet may be in direct contact with the skin of the wearer of the absorbent article when the article is in use, having a high content of natural fibers, such as cotton fibers, in the first layer of the topsheet enables to have a soft feel for the wearer's skin as well as to increase the amount of biodegradable material in contact with the wearer's skin and to decrease the risk of allergies, irritations or rashes on the skin of the wearer.

The first layer may be hydrophilic or hydrophobic. The first layer may be hydrophobic.

In order to have a hydrophobic first layer, a hydrophobic treatment may be applied to the first layer. The hydrophobic treatment may be petrochemical based or, at least to some extent, derived from natural sources. The hydrophobic treatment may be natural.

The hydrophobic treatment may be selected from the group consisting of natural oil, butters or waxes and combination thereof. Some examples, but not limited to, are cotton seed oil, Coconut oil, Avocado oil, Jojoba oil, Castor-seed oil, Soybean oil, Almond oil, Lanolin, Olive oil, Sunflower seed oil, Eucalyptus oil, Shea butter, Cocoa butter, Murumuru butter, Almond butter, Avocado butter, Aloe butter, Mango butter, Beeswax, Soy wax, Candelilla wax, Rice-bran wax, Coconut wax.

The hydrophobic treatment may be used in an amount which increases as the percentage of cotton fibers that is present in the first layer increases. The range of the hydrophobic treatment may be from 0.1 g/m² up to 10 g/m², or from 0.5 g/m² to 4 g/m² basis weight.

The hydrophobic treatment may be water repellent applications, hydrophobic surfactants, such as silicone polymers or polyethers. Examples are Zelan™ R3 from Chemours Company and REPELLAN® T from Pulcra Chemicals.

The first layer may comprise a hydrophobic treatment.

The first layer may comprise land areas between the majority of the apertures.

The contact angle on the land areas of the first layer after a conditioning process may be more than 50° according to the post-conditioning contact angle test method described below. The contact angle on the land areas of the first layer after a conditioning process may be more than 60° according to the post-conditioning contact angle test method.

The hydrophobic treatment may be applied via kiss roll coating, spray, gravure printing, slot coating, dipping or other application processes, known in the art.

The hydrophobic treatment may be applied as such (i.e. pure hydrophobic treatment) or may be first dissolved in a solvent, which is then removed after application, or may be first mixed into water to form an emulsion, which is then removed after application. When the hydrophobic treatment is first mixed into water to form an emulsion, an emulsifying agent may be needed.

The first layer may comprise a mixture of hydrophobic natural fibers and hydrophilic natural fibers. The hydrophobic natural fibers may be hydrophilic natural fibers that are treated with a hydrophobic treatment before forming the first layer.

The amount of hydrophobic natural fibers may be higher than the amount of hydrophilic natural fibers.

For example, the natural fibers comprised by the first layer may comprise a mixture of from 5% to 40% by weight, or from 5% to 30% by weight of hydrophilic natural fibers and from 60% to 95% by weight, or from 30% to 95% by weight of hydrophobic natural fibers by total weight of the first layer. The natural fibers comprised by the first layer may also be 100% by weight of hydrophobic natural fibers.

Alternatively, the first layer may comprise a mixture of hydrophilic fibers selected from the group consisting of synthetic fibers, natural fibers and/or combinations thereof, and hydrophobic natural fibers. The hydrophobic natural fibers may be hydrophilic natural fibers that have been treated with a hydrophobic treatment before forming the first layer.

The amount of hydrophobic natural fibers may be higher than the amount of hydrophilic fibers.

For example, the first layer may comprise a mixture of from 5% to 40% by weight of hydrophilic fibers and from 60% to 95% by weight of hydrophobic natural fibers by total weight of the first layer.

Alternatively, naturally hydrophobic fibers may be used, such as cotton fibers not treated or mildly treated through scouring and/or bleaching. Untreated cotton fibers (i.e. non-bleached or scoured) are hydrophobic due to natural waxes on the fibers. Alternatively, hydrophobic viscose fibers may be used, as known in the art.

The first layer may have a basis weight of from 10 g/m² to 50 g/m², or from 15 g/m² to 40 g/m².

Cross-Lapped Spunlace Nonwoven Layer:

The first layer may be a cross-lapped spunlace nonwoven layer.

The precursor web of the first layer may be, for example, a carded nonwoven web formed by a carding process. Once the fibers web is formed via a carding process, a crosslapper, may be used to form a cross-lapped nonwoven layer. The function of a crosslapper is to accept a lightweight fibrous web and to produce a heavier web by laying the lightweight web in layer During this process, the direction of the fiber web may be altered for instance by 90°. Any crosslapping technology known in the art can be applied to obtain a cross-lapped nonwoven layer. Thereby, a web is obtained which is good mechanical strength in machine direction (MD) and cross-direction (CD).

Then, the fibers of the cross-lapped nonwoven layer may be bonded into a spunlace nonwoven. Hydroentanglement uses high-speed jets of water to strike a web of fibers so that the fibers are bonded to each other. Hydroentanglement may be carried out using a dry-laid (carded or air-laid) fiber webs or wet-laid webs as a precursor web.

At the end of this process, we obtain a cross-lapped spunlace nonwoven layer as a first layer of the topsheet. Thus, the mechanical strength of the first layer of the topsheet may be increased, as typically nonwoven fabrics have certain process-related degree of fibers orientation in machine direction, which leads to higher mechanical strength in MD versus CD.

Hybrid Nonwoven Layer:

Alternatively, the first layer may be a spunlace nonwoven layer composed of a nonwoven carrier web and of a web comprising natural fibers with part of the web comprising natural fibers entering the carrier web.

The web comprising natural fibers may be formed on one side of the carrier web. Natural fibers of the natural fiber web may enter the fiber network of the carrier web and interlace with the fiber network. Understandably, the natural fibers may interlace with each other. The carrier web may also interlace with the web comprising natural fibers.

The carrier web may be made of different types of synthetic fibers. The carrier web may be made also of cellulosic fibers.

Synthetic fibers may be selected from the group consisting of polyesters, polypropylenes, polyethylenes, polyethers, polyamides, polyhydroxyalkanoates, polysaccharides, and combinations thereof. More specifically, Synthetic fibers may be selected from the group consisting of polyethylene terephthalate, polybutylene terephthalate, poly (1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer, polycaprolactone, polyhydroxyl ether ester, polyhydroxyl ether amide, polyesteramide, polylactic acid, polyhydroxybutyrate, and combinations thereof. Additionally, other synthetic fibers such as rayon, polyethylene, and polypropylene fibers can be used within the scope of the present disclosure.

The synthetic fibers may be polypropylene, polyethylene, polyester, polyethylene terephthalate, polybutylene terephthalate, polyamide, polylactic acid, and combinations thereof.

The carrier web may comprise spunbond fibers or carded fibers. The carrier web may be a carded web or a spunbond web.

The web comprising natural fibers may comprise natural fibers selected from the group consisting of cotton fibers, bamboo fibers and mixtures thereof.

The web comprising natural fibers may comprise staple fibers. The natural fibers may be staple fibers.

The web comprising natural fibers may be made of cotton fibers and 0% to 10%, or 1% to 8%, or 1% to 5% by weight of other fibers by total weight of the web comprising natural fibers, such as rayon fiber, pulp fiber, and heat fusible fiber.

The capillary force may gradually increase from the side of the first layer where the web comprising natural fibers is formed to the center of the first layer in the thickness direction. Therefore, the first layer of the topsheet exhibits improved liquid handling properties from the web comprising natural fibers to the inside of the first layer, whereby the side where the web comprising natural fibers is formed provides a dry feel.

Moreover, since part of the web comprising natural fibers enters the carrier web, the web comprising natural fibers has enhanced mechanical strength such as tensile strength, therefore improving the mechanical strength of the topsheet.

The first layer may be a nonwoven layer comprising at least 20% by weight of natural fibers by total weight of the first layer and not more than 80% by weight of synthetic fibers, such as thermoplastic fibers, by total weight of the first layer. The first layer comprises at least 30% by weight of natural fibers by total weight of the first layer and not more than 70% by weight of synthetic fibers, such as thermoplastic fibers, by total weight of the first layer. The first layer may comprise at least 50% by weight of natural fibers by total weight of the first layer and not more than 70% by weight of synthetic fibers, such as thermoplastic fibers, by total weight of the first layer.

The carrier web may be formed via a through air bonding process, an air laying process, a carding process, a spunbond process or other known process in the art to form a nonwoven web. For example, by using a through air bonding process, a mixture of synthetic fibers may be formed into a carrier web with a carding machine and hot air at a predetermined temperature may be blown through the carrier web to fuse the fiber intersections. The carrier web may be conveyed on a wire mesh endless belt.

Separately, a web comprising natural fibers may be obtained by a carding machine for example.

The resulting web comprising natural fibers may be superimposed on the carrier web and water jets from a jet nozzle may be directed to the web comprising natural fibers. When the water jets strike the web, entanglement may occur in the web comprising natural fibers between the natural fibers and the constituent fibers of the carrier web, thus forming the spunlace nonwoven.

The water jets can also be directed to the carrier web or can be directed to both webs.

The Second Layer:

The topsheet comprises a first layer and a second layer. The first layer corresponds to the first layer as described above.

The topsheet has a second layer in a face to face relationship with the first layer as described above.

The second layer may be a woven or nonwoven web of natural fibers, synthetic fibers or a combination of natural and synthetic fibers. The second layer may have no natural fibers or less natural fibers than the first layer, such as at least 10% by weight lower amount of natural fibers than the first layer. The second layer may not have more than 10% by weight, or not more than 5% by weight of natural fibers.

The list of synthetic fibers and of natural fibers corresponds to the list disclosed above for the topsheet.

Several examples of nonwoven materials suitable for use as a topsheet may include, but are not limited to: spunbonded nonwovens; carded nonwovens; carded air through nonwovens; spunlace nonwovens; needle punched nonwovens and nonwovens with relatively specific properties to be able to be readily deformed.

The nonwoven web can be formed from many processes, such as, for example, air laying processes, wetlaid processes, meltblowing processes, spunbonding processes, needle punching processes and carding processes. The fibers in the nonwoven web can then be bonded via spunlacing processes, hydroentangling, calendar bonding, through-air bonding and resin bonding.

The synthetic fibers may be polypropylene, polyethylene, polyester, polyethylene terephthalate, polybutylene terephthalate, polyamide, polylactic acid, and combinations thereof.

The synthetic fibers may be single component fibers, multi-component fibers such as bicomponent fibers and combinations thereof.

The natural fibers may be cotton fibers, bamboo fibers, or mixtures thereof.

The fibers may have any suitable deniers or denier ranges and/or fiber lengths or fiber length ranges.

Structure of the First Layer and of the Second Layer:

The first layer has a first surface and a second surface. The second layer has a first surface and a second surface.

When the topsheet described herein is incorporated into an absorbent article, the first surface of the first layer is facing towards the body of the wearer during use of the article and the second surface of the first layer is facing towards the backsheet of the absorbent article.

The first surface of the second layer may be in contact with the second surface of the first layer.

When the topsheet described herein is incorporated into an absorbent article, the first surface of the second layer is facing towards the body of the wearer during use of the article and the second surface of the second layer is facing towards the backsheet.

When the topsheet described herein is incorporated into an absorbent article, the first layer is facing towards the body of the wearer and the second layer is facing towards the backsheet.

The first layer has a plurality of apertures. The apertures in the first layer of the topsheet play an important role to enable initial and fast fluid flow, especially when the first layer is hydrophobic. Therefore, the first layer of the topsheet which may be hydrophobic works in concert with the apertures to reduce wetness on the wearer-facing surface of the topsheet.

The plurality of apertures may be uniformly distributed on the first layer. To ensure material stability, the smallest distance between the majority of the apertures regardless of their particular shape and size may be at least 0.5 mm, or at least 1.5 mm. This distance is measured on the first surface of the first layer of the topsheet.

The second layer has a plurality of apertures. The second layer has a plurality of apertures at least partially aligned with the apertures of the first layer. The apertures of the first layer correspond to the apertures of the second layer. All apertures of the second layer may be aligned with the apertures of the first layer.

The plurality of apertures of the second layer may be uniformly distributed on the second layer.

The first layer at least partially penetrates the second layer of the topsheet at the apertures.

This characteristic may be facilitated according to the process described below.

Thus, the apertures may extend outward, away from a surface of the first layer. The apertures may extend outward, away from the second surface of the first layer.

Likewise, the apertures may extend outward, away from a surface of the second layer. The apertures may extend outward, away from the second surface of the second layer.

The apertures of the first and second layer extending outwardly, away from the surface of the first or second layer such that the apertures comprise side walls.

Generally, aperturing a spunlace nonwoven weakens the material. However, by having the first layer at least partially penetrating the second layer of the topsheet at the apertures (specifically: at the side walls of the apertures), has a stabilizing effect on the first layer and on the topsheet as a whole. This stabilizing effect further facilitates a stable three-dimensional configuration of the first layer comprising the natural fibers. When using layers comprising substantial amounts of (hydrophilic) natural fibers as skin-contacting layers of a topsheet tends to negatively impact skin dryness. Imparting a three-dimensional configuration reduces contact with the skin. However, if the second layer, underlying the first layer (i.e. being provided away from the skin during use) does not have protrusions, the contact between the first and the second layer is reduced, which creates problems in obtaining sufficient integrity and increases the risk of delamination.

(Partial) penetration of the fibers of the first layer into the second layer at the apertures improves the integrity of the topsheet by reducing the risk of delamination of the first and second layer. Fiber penetration creates "anchor points" which stabilizes the laminate of first and second layer, even if the contact area between first and second layer is reduced as only the first layer has protrusions. The anchor points also reduce the risk of fiber fuzzing.

The side walls of the apertures of the first layer may terminate short of the side walls of the apertures of the second layer in the plurality of apertures. Therefore, at the bottom part of the side wall of the apertures, the apertures may be only formed by the second layer.

The apertures may vary in shape. For example, the shape of the apertures as seen from the first surface of the first layer may be circular, elliptic, rectangular or polygonal. The apertures may have a circular shape, an elliptic shape, or a polygonal shape.

The tridimensional shape of the apertures may be cylindrical (e.g. with a circular or elliptic base), prismatic (e.g. with a polygonal base), truncated cone or pyramidal.

The plurality of apertures of the first layer and of the second layer may be simply holes with no side walls.

When the topsheet described herein is incorporated into an absorbent article, the apertures may extend outwardly away from the topsheet and toward the absorbent core. Alternatively, the apertures may extend away from the absorbent core (i.e. the toward the skin of the wearer, when the article is in use).

The amount of extension of the side walls of the apertures of the first layer and of the second layer should be at least 0.1 mm beyond the first surface of the first layer or at least 0.2 mm beyond the first surface of the first layer. The side walls of the apertures of the first layer and of the second layer may form funnels or channels.

The apertures may comprise side walls having a top part proximate to the first surface and a bottom part proximate to the second surface.

The term "top part of the apertures" means the part of the aperture that is proximate to the first surface of the first layer.

The term "bottom part of the apertures" means the part of the aperture that is proximate to the second surface of the first layer or proximate to the bottom edge of the apertures.

The aperture will be tapered and take a conical shape such that the diameter of the aperture is larger proximate the second surface than the diameter of the opening proximate the bottom edge of the aperture.

Topsheets with apertures generally have an increased risk of rewet, i.e. of liquid passing back components underneath the topsheet (such as the absorbent core) into and through the topsheet. For apertured hydrophobic topsheets (for the present disclosure: when the first layer is hydrophobic), rewet occurs predominantly through the apertures. The tapered shape of the apertures can help to reduce rewet, as the diameter of the apertures toward the absorbent core is smaller than the diameter of the aperture in the first layer. Moreover, if the first layer is hydrophobic, the side walls of the apertures of the hydrophobic first layer overlay the side walls of the second layer (which may be hydrophilic), thus further reducing the risk of liquid passing back through the apertures.

The apertures may also vary in size. Smaller apertures can contribute to lower rewet and generally tend to create less red marking on the skin of the wearer. Hence, the apertures may have a size of 4 mm² or less, of 3.5 mm² or less, of 3.0 mm² or less, or of 2.5 mm² or less. The size of the apertures may not be less than 0.5 mm². The size is determined on the surface which is opposite to the surface from which the apertures extend outwardly away from the surface, i.e. for conical apertures the larger aperture opening is determined.

The first layer comprises also a plurality of protrusions.

The majority of the protrusions may have a first Z-directional height.

The majority of the protrusions may be located on the first surface of the first layer. The majority of the protrusions may extend outward from the first surface of the first layer.

Alternatively, the protrusions may extend outward from the second surface of the first layer. In this case, the protrusions may be named "recesses" as explained below.

The plurality of the protrusions may be uniformly on the first surface of the first layer. The majority of the protrusions may be provided throughout the complete surface of the first layer or may only be provided in a portion of the first layer.

The plurality of apertures is located between the protrusions.

The plurality of protrusions imparts a three-dimensional shape to the first layer.

The majority of the protrusions can be hollow. When viewing from the first surface of the first layer, the majority of the protrusions may protrude from the land areas of the first layer in the same direction.

When the topsheet described herein is incorporated into an absorbent article, the plurality of protrusions may protrude away from the absorbent core of the absorbent article toward the skin of the wearer, when the article is in use.

Alternatively, when the topsheet described herein is incorporated into an absorbent article, the plurality of protrusions may protrude towards the absorbent core of the absorbent article.

Viewed from a cross-sectional view, i.e. in a Z-direction, the majority of the protrusions may have any suitable shapes which include, but are not limited to: cylindrical, bulbous-shaped, conical-shaped and mushroom shaped.

Viewed from above, the majority of the protrusions may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions. The majority of the protrusions may be dome-shaped.

The majority of the protrusions may form, in conjunction, one or more graphics. Having graphics can support the caregiver's perception that the absorbent article is well able to absorb the liquid bodily exudates.

Also, the majority of the protrusions may form, in conjunction, one or more graphics such as a logo, e.g. the Pampers Heart logo.

The majority of the protrusions extending outwardly from the first surface of the first layer may represent at least 20%, at least 30%, at least 40%, at least 50%, at least 70%, at least 80% but not more than 95% of the total area of the first layer of the topsheet.

The majority of the protrusions may have a Z-directional height in the range from about 300 μm to about 6000 μm, from about 500 μm to about 5000 μm, or from about 750 μm to about 3000 μm.

Referring to FIG. 1, the topsheet may comprise a three-dimensional first layer 1 and a second layer 2 free of protrusions. The first layer may comprise a first surface 3 and a second surface 4. The second layer may comprise a first surface 10 and a second surface 11.

The first surface 10 of the second layer 2 may be in contact with the second surface 4 of the first layer 1.

When the topsheet described herein is incorporated into an absorbent article, the first surface 10 of the second layer 2 is facing towards the body of the wearer during use of the article and the second surface 11 of the second layer 2 is facing towards the backsheet.

When the topsheet described herein is incorporated into an absorbent article, the first layer 1 is facing towards the body of the wearer during use of the article and the second layer 2 is facing towards the backsheet.

The second layer 2 has a plurality of apertures 5. The first layer 1 has a plurality of apertures 5.

The apertures may comprise side walls having a top part 6 proximate to the first surface 3 of the first layer 1 and a bottom part 7 proximate to the second surface 4 of the first layer 1.

The second layer 2 has a plurality of apertures 5 at least partially, or completely aligned with the apertures 5 of the first layer 1. The apertures 5 of the first layer 1 and of the second layer 2 may be the same. The plurality of apertures 5 of the second layer 2 may have at least partially the same width and/or length as the apertures 5 of the first layer 1.

The side walls of the apertures in the first layer 1 may be shorter than the side walls of the apertures in the second layer 2. Therefore, at the bottom part of the apertures 5, the apertures 5 may be only formed by the second layer 2.

The first layer may comprise land areas 8 between the majority of, or between all of the apertures 5. The land areas 8 may be substantially flat areas. The land areas 8 may be flat areas.

The land areas 8 may fully surround the apertures 5. The land areas may together form a generally continuous grid through the first layer, while the apertures 5 may be discrete elements throughout the first layer.

The first layer 1 has also a plurality of protrusions 9.

The majority of the protrusions, or all of the protrusions 9 may protrude from the land areas 8 of the first layer 1 of the topsheet 24 forming a base 16 and an opposed distal portion 17 from the land areas 8. The opposed distal portion of the protrusions 9 may extend to a distal end which forms a top peak which is spaced away from the base of the protrusions 9. The base of the majority of the protrusions, or all of the protrusions 9 can be defined as the perimeter, which for circular protrusions, is the circumference, where each protrusion starts to protrude outwardly from the land areas 8 of the first layer 1.

The majority of the protrusions, or all of the protrusions 9 may have a first Z-directional height.

The majority of the protrusions, or all of the protrusions 9 may be located on the first surface 3 of the first layer 1. The majority of the protrusions, or all of the protrusions 9 may extend outward from the first surface 3 of the first layer 1. Alternatively, the protrusions 9 may extend outward from the second surface 4 of the first layer 1. In this case, the protrusions 9 may be named "recesses" as explained below.

The plurality of the protrusions 9 may be uniformly distributed on the first surface 3 of the first layer 1. The majority of the protrusions, or all of the protrusions 9 may be provided throughout the complete surface of the first layer 1 or may only be provided in a portion of the first layer 1.

The majority of the protrusions, or all of the protrusions 9 may be surrounded by a plurality of land areas 8 and/or a plurality of apertures 5. The plurality of apertures 5 are located between the majority of the protrusions, or all of the protrusions 9.

The plurality of protrusions 9 imparts a three-dimensional shape to the first layer 1. The plurality of land areas 8, the plurality of apertures 5 and the plurality of protrusions 9 may form a three-dimensional surface on the first surface 3 of the first layer 1 of the topsheet 24.

Alternatively, the plurality of land areas 8, the plurality of apertures 5 and the plurality of protrusions 9 may form a three-dimensional surface on the second surface 4 of the first layer 1 of the topsheet 24.

The plurality of land areas 8, the plurality of apertures and the plurality of protrusions may impart a three-dimensional shape to the first layer 1 of the topsheet 24.

The majority of the protrusions, or all of the protrusions 9 can be hollow. When viewing from the first surface 3 of the first layer 1, the majority of the protrusions, or all of the protrusions 9 may protrude from the land areas 8 of the first layer 1 in the same direction.

When the topsheet described herein is incorporated into an absorbent article, the plurality of protrusions may protrude away from the absorbent core of the absorbent article.

Alternatively, when the topsheet described herein is incorporated into an absorbent article, the plurality of protrusions may protrude towards the absorbent core of the absorbent article.

Two or more adjacent protrusions 9 may be separated by one or more land areas 8 and/or one or more apertures 5 in a direction generally perpendicular to the longitudinal centerline or in a direction generally parallel to the longitudinal centerline of the first layer 1. The longitudinal centerline of the first layer corresponds to the longitudinal centerline of the absorbent article, when the topsheet is incorporated into an absorbent article.

The majority of the protrusions, or all of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

When the topsheet 24 described herein is incorporated into an absorbent article, the topsheet may be in close contact with underlaying layers such as a distribution layer. The underlaying layers may be made of unconsolidated dry-laid fibers of a dry-laid fibrous structure or a wet-laid fibrous structure. The void volumes 14 of the protrusions 9 can allow feces to be absorbed and acquired within them.

The majority of the protrusions, or all of the protrusions 9 may be defined by a protrusion base width $WB_1$ of the base 16 forming an opening which is measured from two side walls of the inner portion at the base 16. The majority of the protrusions 9 may be defined by a width $WD_2$ of the inside void volume 14 which is the maximum interior width measured between two side walls of the inner protrusion or which is the maximum diameter of the side wall of the inner protrusion when the distal portion 17 has a substantially circular shape. The maximum interior width $WD_2$ of the void volume 14 at the opposed distal portion 17 may be greater than the protrusion base width $WB_1$ of the base 16 of the protrusions 9. The protrusion base width $WB_1$ of the base 16 of the majority of the protrusion 9 may range from 0.5 mm to 15 mm or from 0.5 mm to 10 mm or from 0.5 mm to 5 mm or from 0.5 mm to 3 mm. Measurements of the dimensions of the protrusion base width $WB_1$ of the base 16 and the width $WD_2$ of the distal portion 17 can be made on a photomicrograph.

This three-dimensional first layer of the topsheet provide better softness to the topsheet. It also helps maintain the skin of the wearer away from body fluids in the land areas as the protrusions essentially create a space between the skin of the wearer and the body fluids.

The second layer 2 may comprise land areas 12 between the majority of the apertures 5. The land areas 8 of the first layer 1 may be aligned with the land areas 12 of the second layer 2.

The land areas 8 of the first layer 1 and the land areas 12 of the second layer 2 may fully surround the apertures 5 of the first layer 1 and of the second layer 2.

The land areas 8 of the first layer 1 and the land areas 12 of the second layer 2 may be substantially flat areas. The land areas 8 of the first layer 1 and the land areas 12 of the second layer 2 may be flat areas.

The second layer 2 may be free of protrusions. The area of the first layer which coincides with the protrusions of the first layer, may be substantially flat, or may be flat. When combined with the first layer, a hollow space is formed inside the topsheet between the protrusions of the first layer and the second layer.

The first layer 1 and the second layer 2 may be in contact with each other, and may be joined with each other between the majority of the protrusions, or all of the protrusions 9 of the first layer 1. The first layer and the second layer may be in contact with each other, and may be joined with each other at the land areas (8, 12) and/or at the apertures 5.

The first layer and the second layer may not be in contact in the protrusions areas.

The first layer and the second layer may be joined together or attached to each other through mechanical bonding, adhesive bonding, pressure bonding, heat bonding, passing heated air through both layers, or by other methods of joining to form the topsheet as known in the art.

Especially, when the first layer comprising a relatively high amount of natural fibers, bonding the first and second layer to each other using heat may be difficult. As the natural fibers do not become tacky or melt upon exposure to heat, the first layer may not properly and durably bond to the second layer. The first layer may be attached to the second layer in bonding areas by hot melt adhesive.

The bonding areas may be at the land areas (8, 12) and/or at the apertures 5.

When the first layer is attached to the second layer in bonding areas by hot melt adhesive, the delamination force between the first layer and the second layer may be higher than 0.25 N/(50.8 mm), higher than 0.50 N/(50.8 mm), or higher than 1.00 N/(50.8 mm) according to the delamination force test method described herein below.

When the topsheet as described above is used in an absorbent article and if the delamination force is not high enough, there is a risk that the first layer can be detached from the second layer by the move of the wearer of the absorbent article, especially when the article has been wetted. This may create in-use integrity problems. Therefore, having a delamination force between the first layer and the second layer of the topsheet that is increased allow to have a topsheet that keeps its integrity during in-use conditions.

The first layer and the second layer may be attached to each other with a hot melt adhesive applied in the form of spirals, slot coating or spray. The basis weight of the hot melt adhesive may be of at least 1 $g/m^2$, at least 5 $g/m^2$, or at least 7 $g/m^2$.

The adhesive may be applied on the second layer prior to joining the second layer with the first layer. The hot melt adhesive may not only be applied in the land areas. Instead, the adhesive may also be applied on the second layer in the areas which coincides with the protrusions of the first layer. If the second layer is flat in the areas coinciding with the protrusions of the first layer, a void volume is formed between the second layer and the protrusions of the first layer.

When applying the adhesive, such as hot melt adhesive, also to the flat areas of the second layer which coincide with the protrusions of the first layer, it is critical to select the adhesive such that the adhesive is sufficiently solidified and non-tacky at temperatures typically occurring in use of the absorbent article and during storage of the article (such temperatures may be up to 40° C.). Otherwise, when the absorbent article is compressed, there is a risk that the protrusions bond to the second layer, thus impairing the protrusions. Compression of the absorbent article and of the topsheet will often occur when diapers are compressed within the package after manufacturing prior to opening by the consumer, and when a wearer imparts pressure (e.g. by sitting) during use.

At the same time as being sufficiently non-tacky at storage and in-use conditions, the adhesive, such as hot melt adhesive, must provide a strong bond between the first and second layer to reduce or avoid the risk of delamination during use.

Moreover, the hot melt adhesive may be in contact with the skin of the wearer of the absorbent article via the apertures which may create skin problems.

Accordingly, to address these problems, the hot melt adhesive may have a softening point of more than 60° C., more than 80° C., or more than 90° C. according to the ASTM E28-99 test method. Moreover, the hot melt adhesive may have a storage modulus (G') that is higher than $0.3 \times 10^6$ Pa in the range of 0° C. and 40° C. The hot melt adhesive may have a storage modulus (G') that is higher than $0.3 \times 10^6$ Pa in the range of 0° C. and 50° C. or 0° C. and 60° C. or 0° C. and 70° C. or 0° C. and 80° C. or 0° C. and 90° C., or 0° C. and 100° C.

In other instances, the hot melt adhesive may have a storage modulus (G') that is higher than $1.0 \times 10^6$ Pa in the range of 0° C. and 50° C., in the range or 0° C. and 75° C., or in the range or 0° C. and 100° C. The hot melt adhesive may have a storage modulus (G') that is lower than $2.0 \times 10^8$ Pa at 25° C.

If the hot melt adhesive becomes soft below a temperature of 60° C., the hot melt adhesive will become tacky at room temperature (25° C.) and at atmospheric pressure (760 mmHg; i.e. $1.013 \times 10^5$ Pa) or at body temperature (37° C.) during use of the absorbent article.

The hot melt adhesive may be hydrophilic. The hydrophilic hot melt adhesive may be selected in the group consisting of styrene block copolymers such as Styrene-Butadiene-Styrene (SBS), Styrene-Isoprene-Styrene (SIS), Styrene-Ethylene-Butadiene-Styrene (SEBS), Styrene-Ethylene-Propylene-Styrene (SEPS) and combinations thereof, or other hot melt adhesives known in the art.

Having a hydrophilic hot melt adhesive attaching the first layer and the second layer can help to have a low run-off of liquid. Therefore, the risk of leakage on the rear waist region or on the front waist region of the absorbent article is reduced when the topsheet of the present disclosure is used in an absorbent article.

When the hot melt adhesive is applied in the land areas of the first layer and/or of the second layer, the hot melt adhesive may also reach the top and/or the side walls of the apertures.

In addition to using adhesive, or alternatively to using adhesive, the first layer may be attached to the second layer in bonding areas by embossing or by pin bonding. The term "embossing" means creating bonding points between the first layer and the second layer by heat or pressure for example.

The total embossing/bonding areas may be defined as being between 1% and 20% of the topsheet. It enables to not affect the softness of the material.

The bonding areas may be at the land areas (8, 12) and/or at the apertures 5.

When the first layer is attached to the second layer in bonding areas by embossing, the delamination force between the first layer and the second layer may be higher than 0.25 N/(50.8 mm), higher than 0.50 N/(50.8 mm), or higher than 1.00 N/(50.8 mm) according to the delamination force test method.

When the topsheet as described above is used in an absorbent article and if the delamination force is not high enough, there is a risk that the first layer can be detached from the second layer by the move of the wearer of the absorbent article. This may create in-use integrity problems. Therefore, having a delamination force between the first layer and the second layer of the topsheet that is increased allow to have a topsheet that keeps its integrity during in-use conditions.

Figure 2:
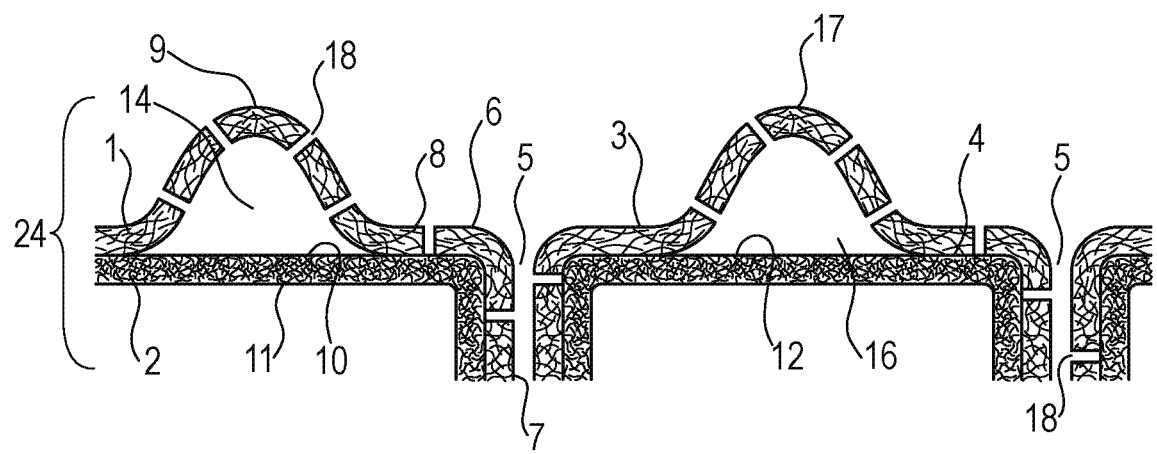
FIG. 2 is another schematic view of a topsheet having a three-dimensional first layer and a second layer free of protrusions in accordance with the present disclosure.

Referring to FIG. 2, the first layer 1 may also comprise a plurality of apertures 18 which are only provided in the first layer and not in the second layer. Alternatively, the first layer may only comprise apertures which are aligned with apertures in the second layer and for which the first layer at least partially penetrates the second layer at the apertures. If the first layer comprises apertures which are not aligned with apertures in the second layer, the dimension of such apertures may be smaller than the apertures in which are aligned with apertures in the second layer.

The apertures 18 may be uniformly distributed along the first surface 3 of the first layer 1.

The plurality of apertures 18, which are only provided in the first layer, may be hydrophilic. A hydrophilic treatment can be applied on the majority of these apertures 18. The hydrophilic treatment may correspond to the same hydrophilic treatment as described above that may be applied on the apertures aligned with apertures in the second layer. The width of the apertures 18, which are only provided in the first layer may be less than 1 mm, or less than 0.5 mm according to the aperture dimension test method.

Alternatively, the apertures 18, which are only provided in the first layer, may be hydrophobic. In such cases, the width of these apertures 18 may be larger than 1 mm, or larger than 1.5 mm according to the aperture dimension test method.

Having a first layer of a topsheet that has a plurality of apertures 18, which are only provided in the first layer, and of apertures which are aligned with the apertures of the second layer allow to have a better absorption of body fluids through the first layer of the topsheet.

Moreover, the mechanical strength of the first layer may be preserved. Indeed, the stress applied to the first layer of the topsheet during the patterning process affects first the apertures which are only in the first layer and not the fibers entanglement of the nonwoven web. The first layer of the topsheet can preserve its strength to a greater extent and reduce fuzzing of short fibers out of the first layer during the patterning process The plurality of apertures, which are only in the first layer may be formed in the first layer before the plurality of apertures which are aligned with apertures in the second layer are formed. Thus, the first layer may be pre-apertured by forming apertures in the first layer. The apertures may be hydrophilic or hydrophobic. The pre-apertured first layer may then go through the processes disclosed below to form a plurality of apertures which are aligned with apertures in the second layer.

The plurality of apertures which are only in the first layer may be formed via the same processes disclosed below to form the plurality of apertures.

Figure 3:
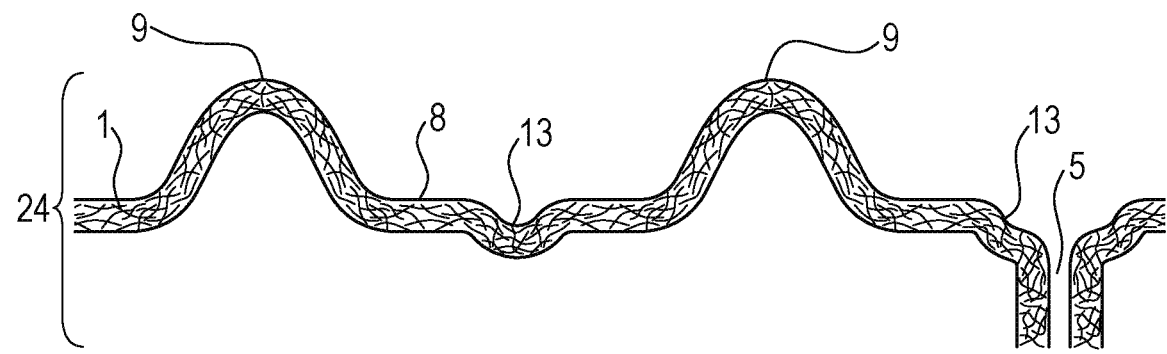
FIG. 3 is a schematic view of a topsheet having a three-dimensional first layer in accordance with the present disclosure.

According to FIG. 3, the first layer 1 of the topsheet 24 may comprise a plurality of protrusions 9 that protrudes outward from the first surface 3 of the first layer 1 or a plurality of recesses 13 that protrudes outward from the second surface 4 of the first layer 1.

Alternatively, the first layer 1 may comprise a plurality of protrusions 9 that protrudes outward from the first surface 3 of the first layer 1 and a plurality of recesses 13 that protrudes outward from the second surface 4 of the first layer 1.

The topsheet 24 of the present disclosure comprises a second layer. The second layer of the topsheet is not represented in this figure.

The term "recesses" corresponds to protrusions of a topsheet that protrude away from the skin of the wearer when the topsheet is incorporated into an absorbent article.

The first layer 1 may comprise a plurality of protrusions 9, a plurality of apertures 5, a plurality of recesses 13 and a plurality of land areas 8.

The plurality of land areas 8, the plurality of recesses 13, the plurality of apertures 5 and the plurality of protrusions 9 may together form a three-dimensional surface on the first side 3 of the first layer 1.

Alternatively, the first layer may comprise a plurality of recesses 13, a plurality of apertures 5 and a plurality of land areas 8. The plurality of land areas 8, the plurality of recesses 13 and the plurality of apertures 5 may together form a three-dimensional surface on the second side 4 of the first layer 1.

The plurality of recesses 13 may be separated by one or more land areas 8, one or more apertures and/or one or more protrusions 9.

The apertures 5 of the first layer may be located between the majority of the recesses 13 of the first layer 1 and/or within the majority of the recesses 13 of the first layer 1. Alternatively, some recesses 13 may not have apertures 5 therein.

The majority of the recesses 13 may define apertures 5 therein at a location most distal from the land areas 8.

The land areas 8 may be positioned intermediate to adjacent protrusions 9, adjacent recesses 13 and/or adjacent apertures 5.

The land areas 8 may form a generally continuous grid through the first layer 1 of the topsheet 24, while the protrusions 9, the apertures and/or the recesses may be discrete elements throughout the first layer 1 of the topsheet 24.

The majority of the recesses may have a Z-directional height in the range from about 200 μm to about 3000 μm, from about 300 μm to about 2000 μm, from about 500 μm to about 1500 μm, or from about 700 μm to about 1000 μm.

The Z-directional height of the protrusions 9 may be equal or higher than the Z-directional height of the recesses 13.
Hydrophobicity/Hydrophilicity of the First Layer:

The first layer may be hydrophobic. The second layer may be hydrophilic.

The contact angle on the first surface of the first layer between the apertures may be more than 70° according to the contact angle test method described herein below.

The contact angle on the second surface of the second layer between the apertures may be less than or equal to 70° according to the contact angle test method.

The difference in contact angle between the first surface of the first layer between the apertures and the contact angle on the second surface of the second layer between the apertures may be at least 10°, or at least 20°.

The width of the apertures 5 of the first layer 1 and of the second layer 2 may be at least 0.8 mm, at least 1 mm, at least 1.5 mm, or at least 2 mm according to the aperture dimension test method described herein below.

Alternatively, the width of the majority of the apertures 5 of the first layer 1 and of the second layer 2 may be less than 1.5 mm, less than 1 mm, or less than 0.5 mm according to the aperture dimension test method. With these apertures having this width, the majority of the apertures 5 of the first layer 1 and of the second layer 2 may be hydrophilic.

A hydrophilic treatment can be applied on the apertures 5. The hydrophilic treatment may be hydrophilic surfactants, such Pluronic® surfactant of BASF, Tetronic® surfactant of BASF and combinations thereof.

The apertures 5 of the first layer 1 and of the second layer 2 may comprise a hydrophilic treatment, i.e. hydrophilic surfactant.

The hydrophilic treatment may be applied to the majority of the apertures during the aperturing pins processes, or via printing processes, or via a hydrophilic hotmelt adhesive between the two layers of the topsheet.

At least 20% of the total apertures of the first layer and of the second layer may be hydrophilic, at least 30% of the total apertures of the first layer and of the second layer may be hydrophilic, or at least 50% of total apertures of the first layer and of the second layer may be hydrophilic. 100% of the total apertures of the first layer and of the second layer may be hydrophilic.

The contact angle on the majority of the apertures, or all of the apertures may be less than or equal to 70° according to the contact angle test method. Specifically, the contact angle on the top part and bottom part of the majority of the apertures may be less than or equal to 70° according to the contact angle test method.

On another side, the first layer may be hydrophobic. The second layer may be hydrophobic.

A hydrophobic treatment may be applied to the second layer. The hydrophobic treatment may be chosen in the list of hydrophobic treatment disclosed above for the first layer. The second layer may comprise a hydrophobic surfactant.

The hydrophobic treatment may be applied via kiss roll coating, spray, gravure printing, slot coating and the other application processes, known in the art.

The contact angle on the first surface of the first layer between the majority of the apertures may be more than 70° according to the contact angle test method.

The contact angle on the second surface of the second layer between the majority of the apertures may be more than 70° according to the contact angle test method.

The width of the majority of the apertures 5 of the first layer 1 and of the second layer 2 may be at least 0.8 mm, at least 1 mm, at least 1.5 mm, or at least 2 mm according to the aperture dimension test method.

Alternatively, the width of the majority of the apertures 5 of the first layer 1 and of the second layer 2 may be less than 1.5 mm, less than 1 mm, or less than 0.5 mm according to the aperture dimension test method. With the apertures having this width, the majority of the apertures may be hydrophilic as described above.

Alternatively, the first layer may be hydrophilic. The second layer may be hydrophilic or hydrophobic.

The contact angle on the first surface of the first layer between the majority of the apertures may be less than or equal to 70° according to the contact angle test method. The contact angle on the second surface of the first layer between the majority of the apertures may be less than or equal to 70° according to the aperture dimension test method.

The width of the majority of the apertures may be less than 1.5 mm, less than 1 mm, or less than 0.5 mm according to the aperture dimension test method.

Therefore, the topsheet as described above provides improved fluid handling properties such as reduced rewet onto the wearer-facing surface of the absorbent article and better liquid acquisition.

Parameters of the Topsheet:

The first layer has a minimum CD strength of at least 3N/(5 cm) according to the tensile strength test method. The first layer may have a minimum CD strength of 5 N/(5 cm) according to the tensile strength test method. The first layer may have a minimum CD strength of 8 N/(5 cm) according to the tensile strength test method.

With the topsheet of the present disclosure, the structural and mechanical strength of the topsheet is increased. During the patterning processes, the topsheet as described above is not damaged and does not create fuzz of natural fibers and/or synthetic fibers. The risk of having irritations and rashes on the skin of the wearer of the absorbent article is decreased.

The topsheet of the present disclosure has a run-off of less than 40% according to the run-off test method. The topsheet may have a run-off of less than 20% according to the run-off test method. The topsheet may have a run-off of less than 15% according to the run-off test method.

The run-off test method reproduces the in-use condition when a wearer of absorbent article discharges body fluids, such as urine or feces on the topsheet of an absorbent article. When the run-off is high, it means that the exuded body fluids are not absorbed by the topsheet and create leakage, for example on the rear waist region of the absorbent article or on the front waist region of the absorbent article.

With the topsheet of the present disclosure, the run-off of body fluid is low, therefore, the risk of leakage on the rear waist region or on the front waist region of the absorbent article is reduced when the topsheet of the present disclosure is used in an absorbent article.

Figure 4:
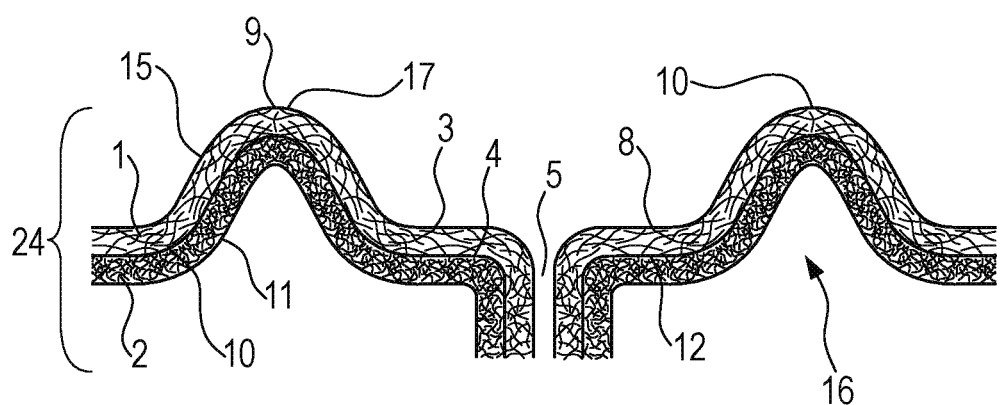
FIG. 4 is a schematic view of a three-dimensional topsheet having a first layer and a second layer in accordance with the present disclosure.

Three-Dimensional Topsheet:

Referring to FIG. 4, the topsheet 24 may be a laminate comprising the first layer 1 as previously described and a second layer 2 as previously described in a face to face relationship. In other words, the first layer 1 and the second layer 2 are joined to form a laminate.

The first layer 1 may have a first surface 3 and a second surface 4. The second layer 2 may have a first surface 10 and a second surface 11.

The first layer 1 and the second layer 2 are aligned in a face to face relationship such that the second surface 4 of the first layer 1 is in contact with the first surface 10 of the second layer 2.

When the topsheet described herein is incorporated into an absorbent article, the first layer 1 is facing towards the body of the wearer and the second layer 2 is facing towards the backsheet.

The first layer 1 and the second layer 2 can be simultaneously mechanically deformed and combined together to provide the topsheet having protrusions. This means that both the first layer 1 and the second layer 2 can be mechanically deformed and combined together at the same time.

The first layer 1 comprises a plurality of protrusions 9. The second layer may comprise a plurality of protrusions 9.

The plurality of protrusions 9 of the first layer may be at least partially aligned, or may be fully aligned with the plurality of protrusions 9 of the second layer 2. The protrusions 9 of the first layer 1 and of the second layer 2 may be the same.

The protrusions 9 are formed from fibers of the first layer 1 and may also be, at least partly, formed of the second layer 2 of the topsheet 24.

If the second layer comprises protrusions as well, the plurality of protrusions 9 imparts a three-dimensional shape to the second layer 2. At the same time, the plurality of protrusions 9 imparts a three-dimensional shape to the first layer 1. The topsheet 24 may be a three-dimensional topsheet.

As shown in FIG. 4, the majority of the protrusions 9 may comprise a base 16 forming an opening and having a protrusion base width, an opposed distal portion 17, and one or more side walls 15 between the base 16 and the opposed distal portion 17 of the majority of the protrusions 9. The base 16, the distal portion 17 and the one or more side walls 15 may be formed by fibers such that the majority of the protrusions 9 has only opening at the base 16.

The majority of the protrusions 9 extending outwardly from the first surface 3 of the first layer 1 may represent at least 20%, at least 30%, at least 40%, at least 50%, at least 70%, at least 80% but not more than 95% of the total area of the first layer 1 of the topsheet 24.

The second layer 2 has a plurality of apertures 5. The first layer 1 has a plurality of apertures 5. The apertures 5 may have a top part and a bottom part.

The second layer 2 has a plurality of apertures 5 at least partially aligned with the apertures 5 of the first layer 1. The apertures 5 of the first layer 1 and of the second layer 2 may be the same. The plurality of apertures 5 of the second layer 2 may have the same width and/or length as the apertures 5 of the first layer 1.

The first layer 1 may be shorter than the second layer 2 in the plurality of apertures 5. Therefore, at the bottom part of the apertures 5, the apertures 5 may be only formed by the second layer 2.

The first layer 1 may comprise land areas 8 that may be substantially flat areas. The land areas 8 may be flat areas. The second layer 2 may comprise land areas 12 that may be substantially flat areas. The land areas 12 may be flat areas. The land areas 8 of the first layer 1 may be aligned with the land areas 12 of the second layer 2. The second layer may also have flat land areas which are aligned with the protrusions of the first layer.

The majority of the protrusions 9 may protrude from the land areas 8 of the first layer 1 and from the land areas 12 of the second layer 2.

The majority of the protrusions 9 may be surrounded by a plurality of land areas (8, 12) and/or by a plurality of apertures 5.

The plurality of the protrusions 9 may be uniformly distributed along the first surface 3 of the first layer 1.

The majority of the protrusions 9 can be hollow. When viewing from the first surface 3 of the first layer 1, the majority of the protrusions 9 may protrude from the land areas 8 of the first layer 1 in the same direction.

When the topsheet described herein is incorporated into an absorbent article, the plurality of protrusions may protrude away from the absorbent core of the absorbent article.

Alternatively, when the topsheet described herein is incorporated into an absorbent article, the plurality of protrusions may protrude towards the absorbent core of the absorbent article.

Viewed from a cross-sectional view, i.e. in a Z-direction, the majority of the protrusions 9 may have any suitable shapes which include, but are not limited to: cylindrical, bulbous-shaped, conical-shaped and mushroom shaped.

Viewed from above, the majority of the protrusions 9 may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions. The majority of the protrusions may have a dome-shape.

The majority of the protrusions 9 may form, in conjunction, one or more graphics. Having graphics can support the caregiver's perception that the absorbent article is well able to absorb the liquid bodily exudates.

Also, the majority of the protrusions 9 may form, in conjunction, one or more graphics such as a logo, e.g. the Pampers Heart logo.

The majority of the protrusions 9 may be made from engaging the first layer 1 with the second layer 2 such as the first layer 1 and the second layer 2 coincide with and fit together.

The first layer and the second layer may be joined together or attached to each other through mechanical bonding, adhesive bonding, pressure bonding, heat bonding, passing heated air through both layers, or by other methods of joining to form the topsheet as known in the art.

The first layer may be attached to the second layer in bonding areas by hot melt adhesive as described above.

The bonding areas may be at the land areas (8, 12) and/or at the apertures 5.

When the first layer is attached to the second layer in bonding areas by hot melt adhesive, the delamination force between the first layer and the second layer may be higher than 0.25 N/(50.8 mm), higher than 0.50 N/(50.8 mm), or higher than 1.00 N/(50.8 mm) according to the delamination force test method.

The first layer may be attached to the second layer in bonding areas by embossing or pin bonding. The term "embossing" means creating bonding points between the first layer and the second layer by heat or pressure for example.

The total embossing/bonding areas may be defined as being between 1% and 20% of the topsheet. It enables to not affect the softness of the material.

The bonding areas may be at the land areas (8, 12) and/or at the apertures 5.

When the first layer is attached to the second layer in bonding areas by embossing, the delamination force between the first layer and the second layer may be higher than 0.25 N/(50.8 mm), higher than 0.50 N/(50.8 mm), or higher than 1.00 N/(50.8 mm) according to the delamination force test method.

When the topsheet as described above is used in an absorbent article and if the delamination force is not high enough, there is a risk that the first layer can be detached from the second layer by the move of the wearer of the absorbent article. This may create in-use integrity problems. Therefore, having a delamination force between the first layer and the second layer of the topsheet that is increased allow to have a topsheet that keeps its integrity during in-use conditions.

The majority of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

When the topsheet 24 described herein is incorporated into an absorbent article, the topsheet may be in close contact with underlaying layers such as a distribution layer. The underlaying layers may be made of unconsolidated dry-laid fibers of a dry-laid fibrous structure or a wet-laid fibrous structure. The void volumes 14 of the protrusions 9 can allow feces to be absorbed and acquired within them.

The majority of the protrusions 9 may be defined by a protrusion base width $WB_1$ of the base 16 forming an opening which is measured from two side walls of the inner portion at the base 16. The majority of the protrusions 9 may be defined by a width $WD_2$ of the inside void volume 14 which is the maximum interior width measured between two side walls of the inner protrusion or which is the maximum diameter of the side wall of the inner protrusion when the distal portion 17 has a substantially circular shape. The maximum interior width $WD_2$ of the void volume 14 at the opposed distal portion 17 may be greater than the protrusion base width $WB_1$ of the base 16 of the protrusions 9. The protrusion base width $WB_1$ of the base 16 of the majority of the protrusion 9 may range from 0.5 mm to 15 mm or from 0.5 mm to 10 mm or from 0.5 mm to 5 mm or from 0.5 mm to 3 mm. Measurements of the dimensions of the protrusion base width $WB_1$ of the base 16 and the width $WD_2$ of the distal portion 17 can be made on a photomicrograph.

The first layer 1 and the second layer 2 may comprise a plurality of protrusions 9 that protrudes outward from the first surface 3 of the first layer 1 or a plurality of recesses that protrudes outward from the second surface 11 of the second layer 2.

Alternatively, the first layer 1 and the second layer 2 may comprise a plurality of protrusions 9 that protrudes outward from the first surface 3 of the first layer 1 and a plurality of recesses that protrudes outward from the second surface 11 of the second layer 2.

The term "recesses" corresponds to protrusions of a topsheet that protrude away from the skin of the wearer when the topsheet is incorporated into an absorbent article.

The first layer 1 and the second layer 2 may comprise a plurality of recesses, a plurality of apertures 5, a plurality of protrusions 9 and a plurality of land areas (8,12).

Alternatively, the first layer 1 and the second layer 2 may comprise a plurality of recesses, a plurality of apertures 5 and a plurality of land areas (8,12).

The apertures 5 may be located between the majority of the recesses and/or within the majority of recesses. Some recesses may not have apertures 5 therein.

The majority of the recesses may define apertures 5 therein at a location most distal from the land areas (8,12).

The land areas (8,12) may be positioned intermediate to adjacent protrusions 9, adjacent recesses and/or adjacent apertures 5.

The plurality of recesses may be separated by one or more land areas (8,12), one or more apertures and/or one or more protrusions 9.

The plurality of recesses of the first layer may be aligned with the plurality of recesses of the second layer. The plurality of recesses of the first layer and of the second layer may be the same.

The first layer and the second layer may be in contact with each other at the recesses.

The majority of the recesses may have a Z-directional height in the range from about 200 μm to about 3000 μm, from about 300 µm to about 2000 µm, from about 500 µm to about 1500 µm, or from about 700 µm to about 1000 µm.

The Z-directional height of the protrusions 9 may be equal or higher than the Z-directional height of the recesses.

On one side, the first layer may be hydrophobic. The second layer may be hydrophilic.

The contact angle on the first surface of the first layer between the majority of the apertures may be more than 70° according to the contact angle test method.

The contact angle on the second surface of the second layer between the majority of the apertures may be less than or equal to 70° according to the contact angle test method. The width of the majority of the apertures 5 of the first layer 1 and of the second layer 2 may be at least 0.8 mm, at least 1 mm, at least 1.5 mm, or at least 2 mm according to the aperture dimension test method.

Alternatively, the width of the majority of the apertures 5 of the first layer 1 and of the second layer 2 may be less than 1.5 mm, less than 1 mm, or less than 0.5 mm according to the aperture dimension test method. With these apertures having this width, the majority of the apertures 5 of the first layer 1 and of the second layer 2 may be hydrophilic.

A hydrophilic treatment can be applied on the majority of the apertures 5. The hydrophilic treatment may be hydrophilic surfactants, such Pluronic® surfactant of BASF, Tetronic® surfactant of BASF and combinations thereof.

The majority of the apertures 5 of the first layer 1 and of the second layer 2 may comprise a hydrophilic surfactant.

The hydrophilic treatment may be applied to the majority of the apertures via the aperturing pins processes as explained above, or via printing processes, or via a hydrophilic hotmelt adhesive between the two layers of the topsheet.

At least 40% of the total apertures of the first layer and of the second layer may be hydrophilic, at least 50% of the total apertures of the first layer and of the second layer may be hydrophilic, or at least 60% of total apertures of the first layer and of the second layer are hydrophilic. 100% of the total apertures of the first layer and of the second layer may be hydrophilic.

The contact angle on the majority of the apertures may be less than or equal to 70° according to the contact angle test method. Specifically, the contact angle on the top part and bottom part of the majority of the apertures may be less than or equal to 70° according to the contact angle test method.

On another side, the first layer may be hydrophobic. The second layer may be hydrophobic.

A hydrophobic treatment may be applied to the second layer. The hydrophobic treatment may be chosen in the list of hydrophobic treatment disclosed above for the first layer. The second layer may comprise a hydrophobic surfactant.

The hydrophobic treatment may be applied via kiss roll coating, spray, gravure printing, slot coating and the other application processes, known in the art.

The contact angle on the first surface of the first layer between the majority of the apertures may be more than 70° according to the contact angle test method.

The contact angle on the second surface of the second layer between the majority of the apertures may be more than 70° according to the contact angle test method.

The width of the majority of the apertures 5 of the first layer 1 and of the second layer 2 may be at least 0.8 mm, at least 1 mm, at least 1.5 mm, or at least 2 mm according to the aperture dimension test method.

Alternatively, the width of the majority of the apertures 5 of the first layer 1 and of the second layer 2 may be less than 1.5 mm, less than 1 mm, or less than 0.5 mm according to the aperture dimension test method. With the apertures having this width, the majority of the apertures may be hydrophilic as described above.

Alternatively, the first layer may be hydrophilic. The second layer may be hydrophilic or hydrophobic.

The contact angle on the first surface of the first layer between the majority of the apertures may be less than or equal to 70° according to the contact angle test method. The contact angle on the second surface of the first layer between the majority of the apertures may be less than or equal to 70° according to the contact angle test method.

The width of the majority of the apertures may be less than 1.5 mm, less than 1 mm, or less than 0.5 mm according to the aperture dimension test method.

Therefore, the topsheet as described above provides improved fluid handling properties such as reduced rewet onto the wearer-facing surface of the absorbent article and better liquid acquisition.

The Mechanical Deformations, the Resulting Protrusions and the Apertures:

The three-dimensional, apertured, first layer of the topsheet of the present disclosure or the laminate of the first layer and the second layer of the topsheet of the present disclosure may be industrially produced at high speed as described below.

Figure 5:
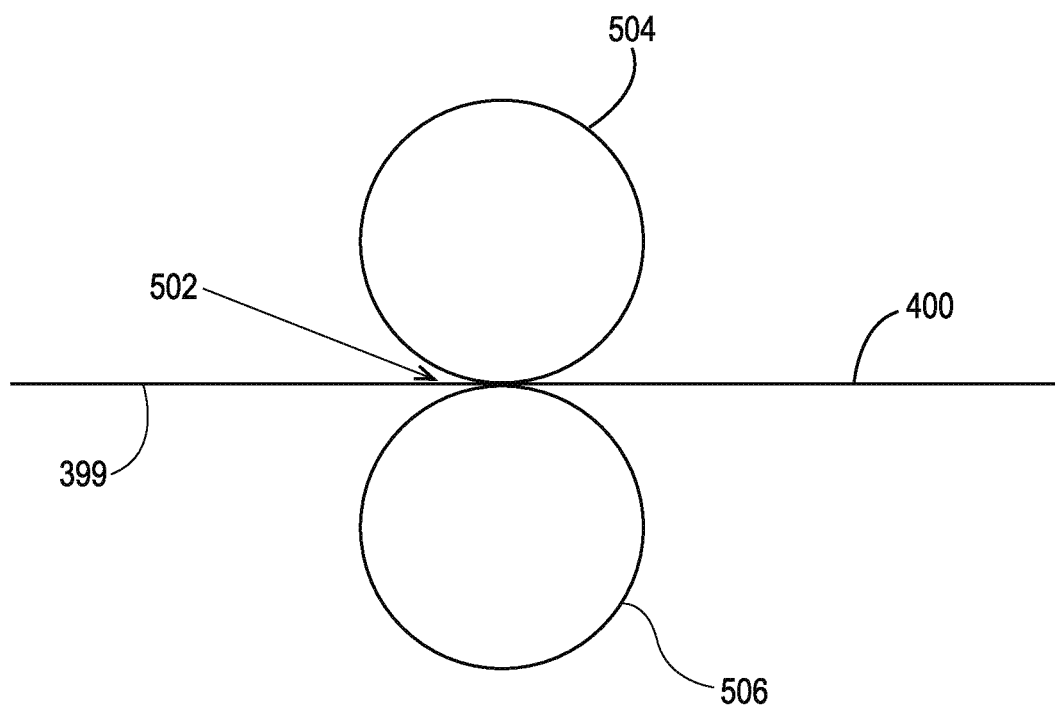
FIG. 5 is a schematic illustration of a first example process for forming the topsheet of the present disclosure.
Figure 6:
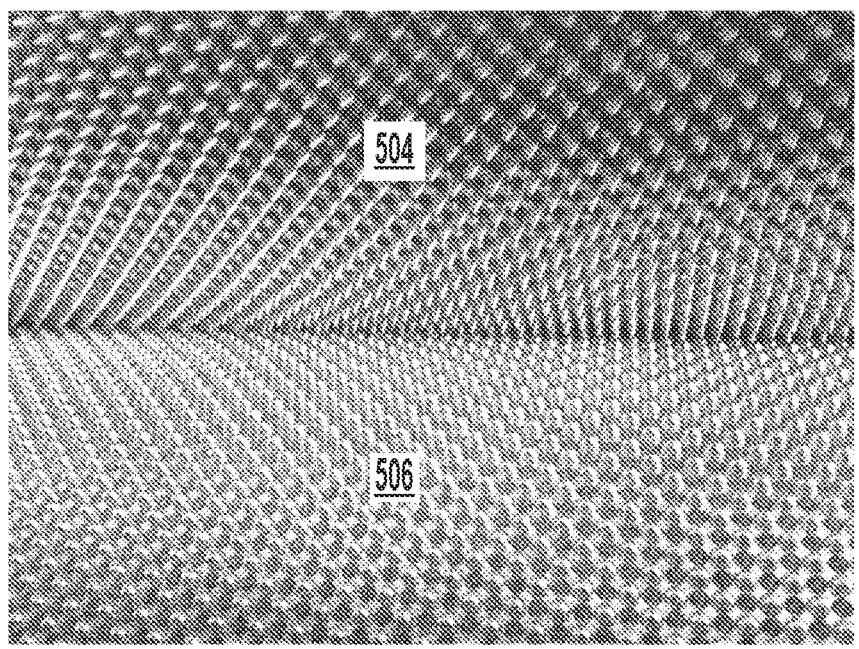
FIG. 6 is a view of intermeshing engagement of portions of first and second rolls in accordance with the present disclosure.
Figure 7:
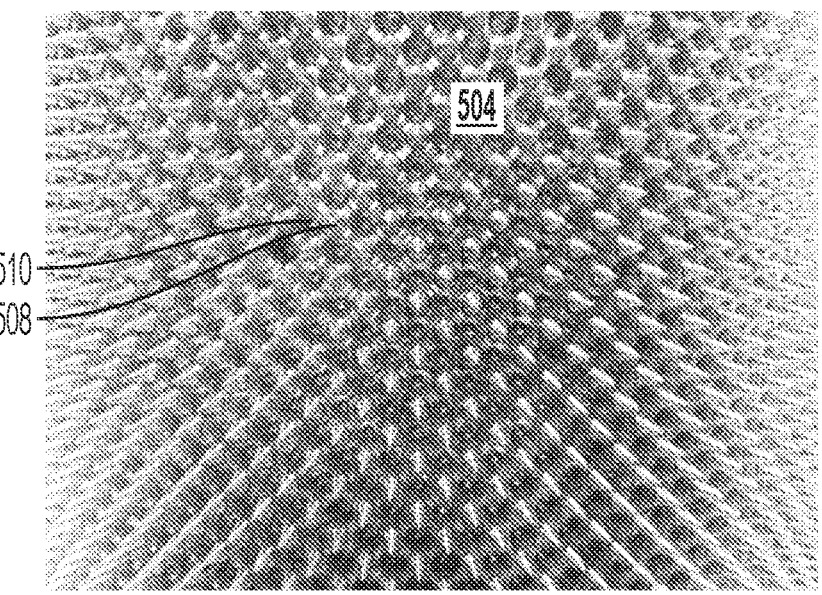
FIG. 7 is a view of a portion of the first roll in accordance with the present disclosure.
Figure 8:
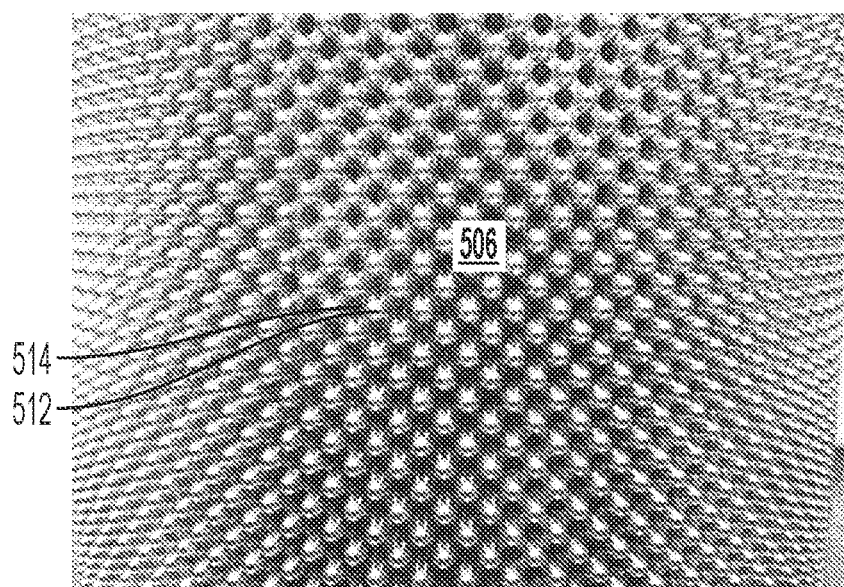
FIG. 8 is a view of a portion of the second roll in accordance with the present disclosure.

FIG. 5 is a schematic illustration of one example process for forming the substrates of the present disclosure. FIG. 6 is a view of intermeshing engagement of portions of first and second rolls. FIG. 7 is a view of a portion of the first roll. FIG. 8 is a view of a portion of the second roll.

Referring to FIGS. 5-8, the first layer of the topsheet of the present disclosure may be formed by passing one or more layer substrate 399 (non-three dimensional) through a nip 502 formed by two intermeshing rolls 504 and 506 to form a three-dimensional substrate 400. The rolls 504 and 506 may be heated. A first roll 504 may create the apertures in the substrate 400 (in combination with the second roll) and a second roll 506 may create the protrusions in the substrate 400 (in combination with the first roll). The first roll 504 may comprise a plurality of protrusions 508 extending radially outwardly from the first roll 504. The first roll 504 may also comprise a plurality of recesses 510 formed in a radial outer surface of the first roll 504. The second roll 506 may comprise a plurality of protrusions 512 extending radially outwardly from the second roll 506. The second roll 506 may also comprise a plurality of recesses 514 formed in the radial outer surface of the second roll 506. The protrusions 508 on the first roll 504 may have a different size, shape, height, area, width and/or dimension than the protrusions 512 on the second roll 506. The recesses 510 formed in the first roll 504 may have a different size, shape, height, area, width, and/or dimension than the recesses 514 formed in the second roll 506. The recesses 510 in the first roll 504 may be configured to at least partially receive the protrusions 512, thereby creating the protrusions in the substrate 400. Specifically, as the protrusions 512 engage into the recesses 510, there is sufficient depth left in the space between the surfaces in a radial direction so that the thickness of the substrate in the protrusions is higher than the thickness of the recesses. This feature provides protrusions with a softer feel and a greater height compared to compressing the portions of the substrate forming the protrusions. The recesses 514 in the second roll 506 may be configured to at least partially receive the protrusions 508 thereby creating the apertures in the first layer of the topsheet.

Alternatively, another method may be used to form the three-dimensional, apertured, first layer of the topsheet of the present disclosure or the laminate of the first and second layer of the topsheet of the present disclosure.

Figure 9:
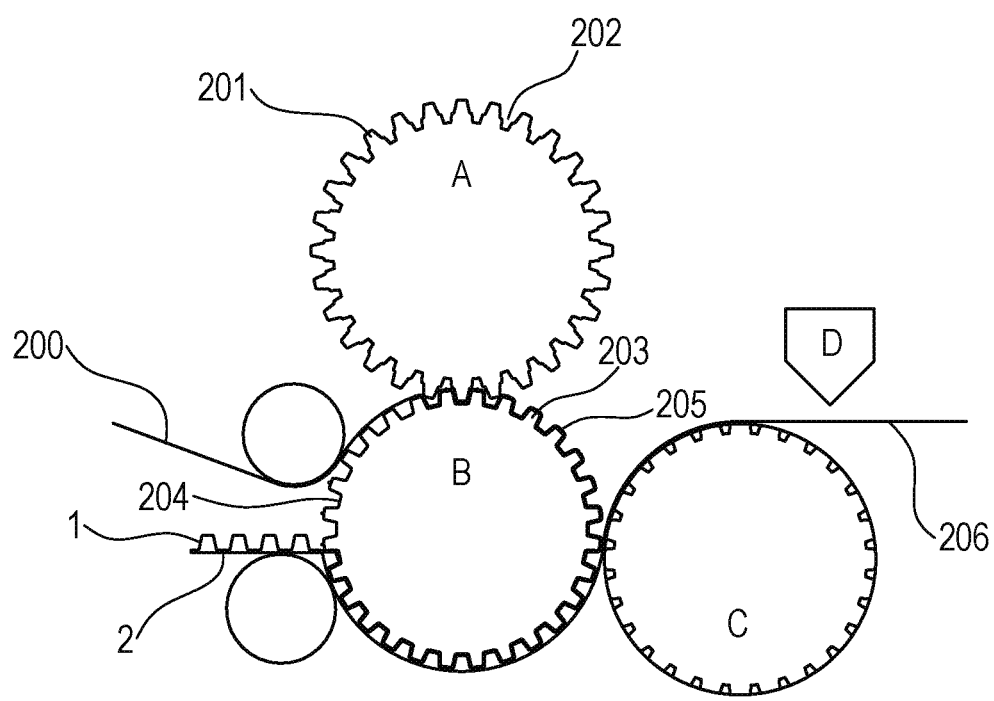
FIG. 9 is a schematic illustration of a second example process for forming the topsheet of the present disclosure.

Referring to FIG. 9, a first substrate 200 may go through a pair of rolls named A and B in order to form the first layer 1 of the present disclosure. The speed of the roll A and B may be from 5 to 600 meters/minute. The temperature range of the roll A may be from 40 to 200° C. The temperature range of the roll B may be from 30 to 200° C. The roll A may comprise a plurality of protrusions 201 extending radially outwardly from the roll A. The roll A may also comprise a plurality of recesses 202 formed in a radial outer surface of the roll A. The depth of the recesses 202 of the roll A may be from 0.5 to 10 mm, the depth of the protrusions 201 of the roll A may be from 0.5 to 9 mm. The roll B may comprise a plurality of protrusions 203 extending radially outwardly from the roll B. The roll B may also comprise a plurality of recesses 204 formed in a radial outer surface of the roll B. The distal end of the plurality of protrusions 203 of the roll B may have the shape of a pin 205.

The protrusions 201 on the roll A may have a different size, shape, height, area, width and/or dimension than the protrusions 203 on the roll B. The recesses 202 formed in the roll A may have a different size, shape, height, area, width, and/or dimension than the recesses 204 formed in the roll B. The recesses 202 in the roll A may be configured to at least partially receive the protrusions 203 of the roll B, thereby creating the protrusions in the first substrate 200. The roll A may comprise a plurality of holes in the recesses area in order to receive the shape of pin 205 of the protrusions 203 of the roll B. Therefore, a plurality of apertures 5 are formed in the first substrate 200 between each two adjacent protrusions of the first substrate 200. The first substrate 200, after going through the roll A and the roll B may comprise a plurality of protrusions 9 and a plurality of apertures 5 between each two adjacent protrusions.

A second substrate 206 may be brought by a concave roller C. Hot melt adhesive may be added on the first surface of the second substrate 206 by an equipment D before the second substrate 206 is in contact with the first substrate 200. The roll C may comprise a plurality of holes in order to receive the shape of pin 205 of the protrusions 203 of the roll B.

The second substrate 206 may pass through the roll C and the roll B and may be in contact with the first substrate 200 at the protrusions 203 of the roll B. As the protrusions 203 of the roll B may have the shape of a pin, a plurality of apertures may be created also on the second substrate 206. The plurality of apertures 5 of the second substrate 206 may be at least partially aligned with the apertures 5 of the first substrate 200.

At the end of the process, a three-dimensional, apertured first layer 1 may be obtained and may be in contact with a second layer 2 between the majority of the protrusions 9 of the first layer. The first substrate 200 may also be the first layer 1 and the second layer 2 engaged together between the rolls A and B, simultaneously mechanically deformed and combined together to form the three-dimensional topsheet 24 of the present disclosure.

In order to form a first layer of a topsheet with a plurality of protrusions, the first layer 1 may be engaged between a first and second forming members and be mechanically deformed to form a first layer with a three-dimensional shape. This method has been described in the PCT application WO2017/156203, published on the 14th of Sep. 2017 and filed by the Procter and Gamble Company, incorporated herein by reference. The first layer may comprise thus deformations forming protrusions 9.

Alternatively, in order to form a three-dimensional topsheet 24 having a first layer 1 and a second layer 2, the first layer 1 and the second layer 2 may be engaged together between a first and second forming members and be simultaneously mechanically deformed and combined together to form the topsheet 24. This method has been described in the PCT application WO2017/156203, published on the 14th of Sep. 2017 and filed by the Procter and Gamble Company, incorporated herein by reference. The topsheet may comprise thus deformations forming protrusions 9.

Moreover, a plurality of different methods known in the art may be used to create an apertured nonwoven, i.e. an apertured topsheet of the present disclosure and to create a three-dimensional nonwoven material with apertures. These methods have been described in the PCT application WO2017/156200, published on the 14th of Sep. 2017 and filed by the Procter and Gamble Company, incorporated herein by reference.

Absorbent Articles:

A typical disposable absorbent article, in which the topsheet of the present disclosure can be used, is placed against or in proximity to the body of the wearer to absorb and contain the various exudates discharged from the body and is represented in FIG. 10 to FIG. 14 in the form of a diaper 20.

Figure 10:
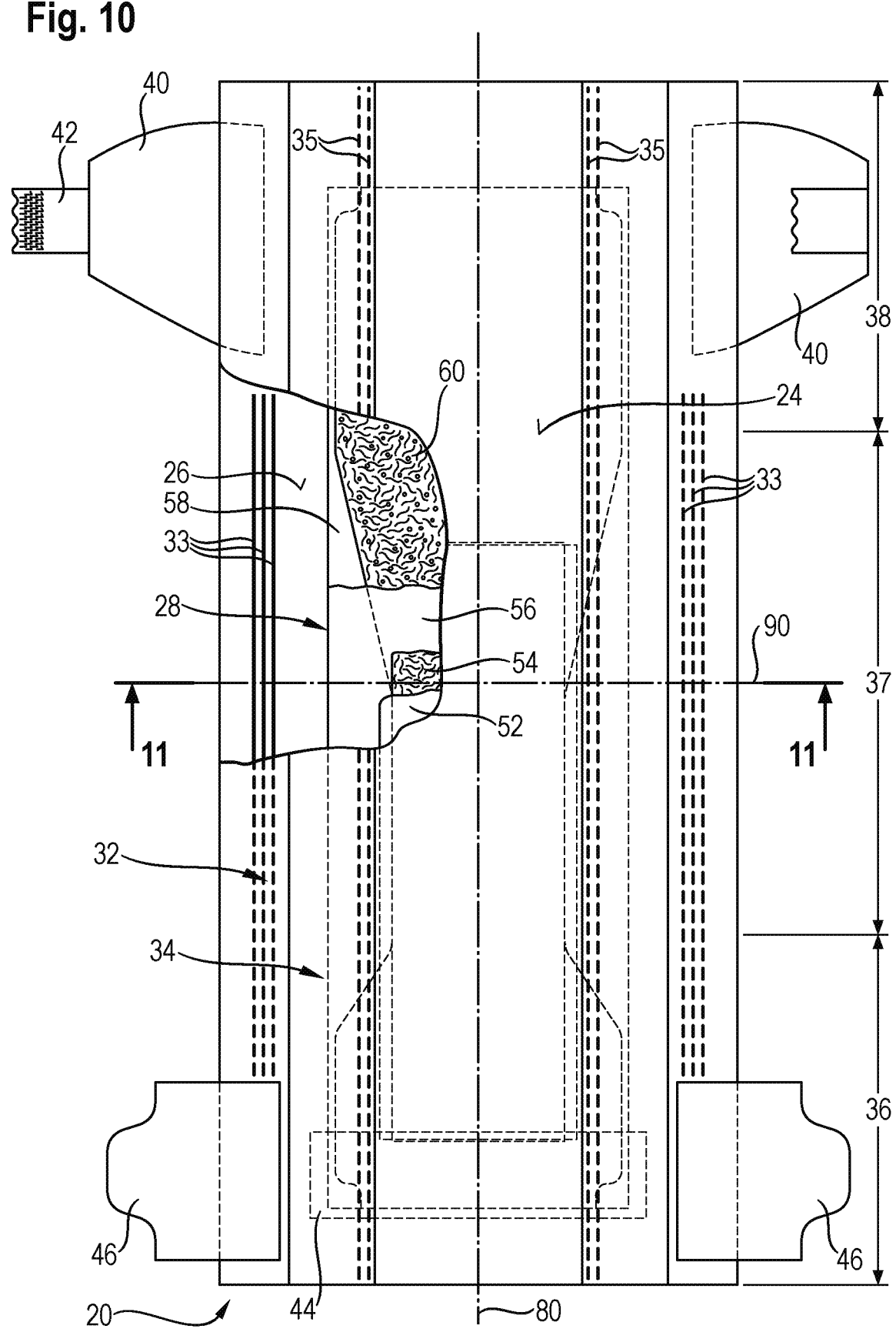
FIG. 10 is a top view of an exemplary absorbent article in the form of a diaper, which may comprise the topsheet of the present disclosure, with some layers partially removed.

In more details, FIG. 10 is a plan view of an exemplary diaper 20, in a flat-out state, with portions of the diaper being cut-away to more clearly show the construction of the diaper 20. This diaper 20 is shown for illustration purpose only as the structure of the present disclosure may be comprised in a wide variety of diapers or other absorbent articles.

Figure 11:
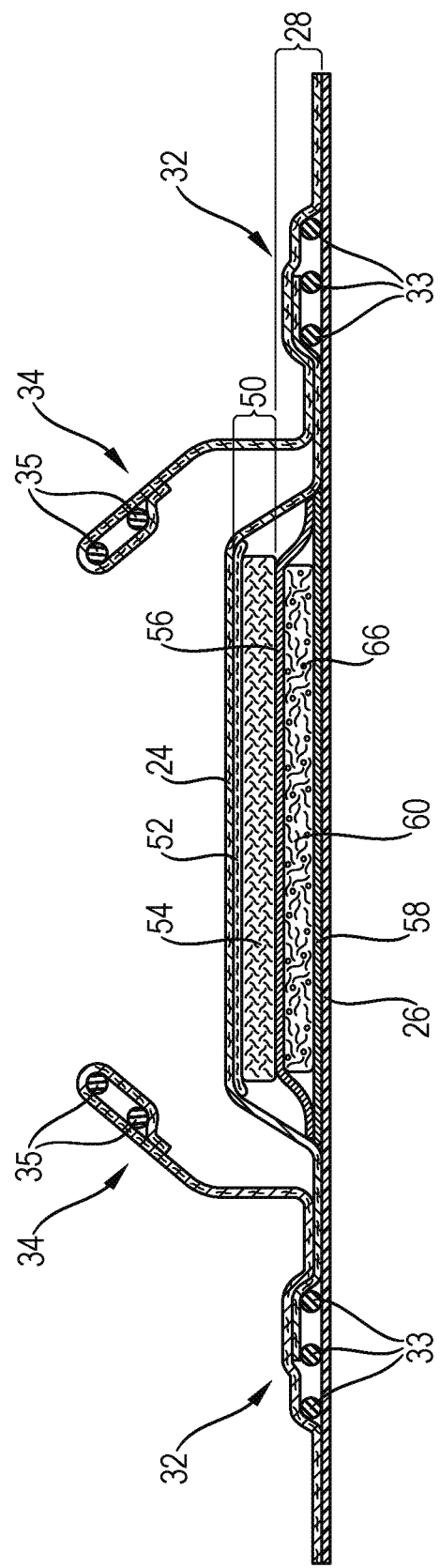
FIG. 11 is a transversal cross-section of the diaper of FIG. 10.
Figure 12:
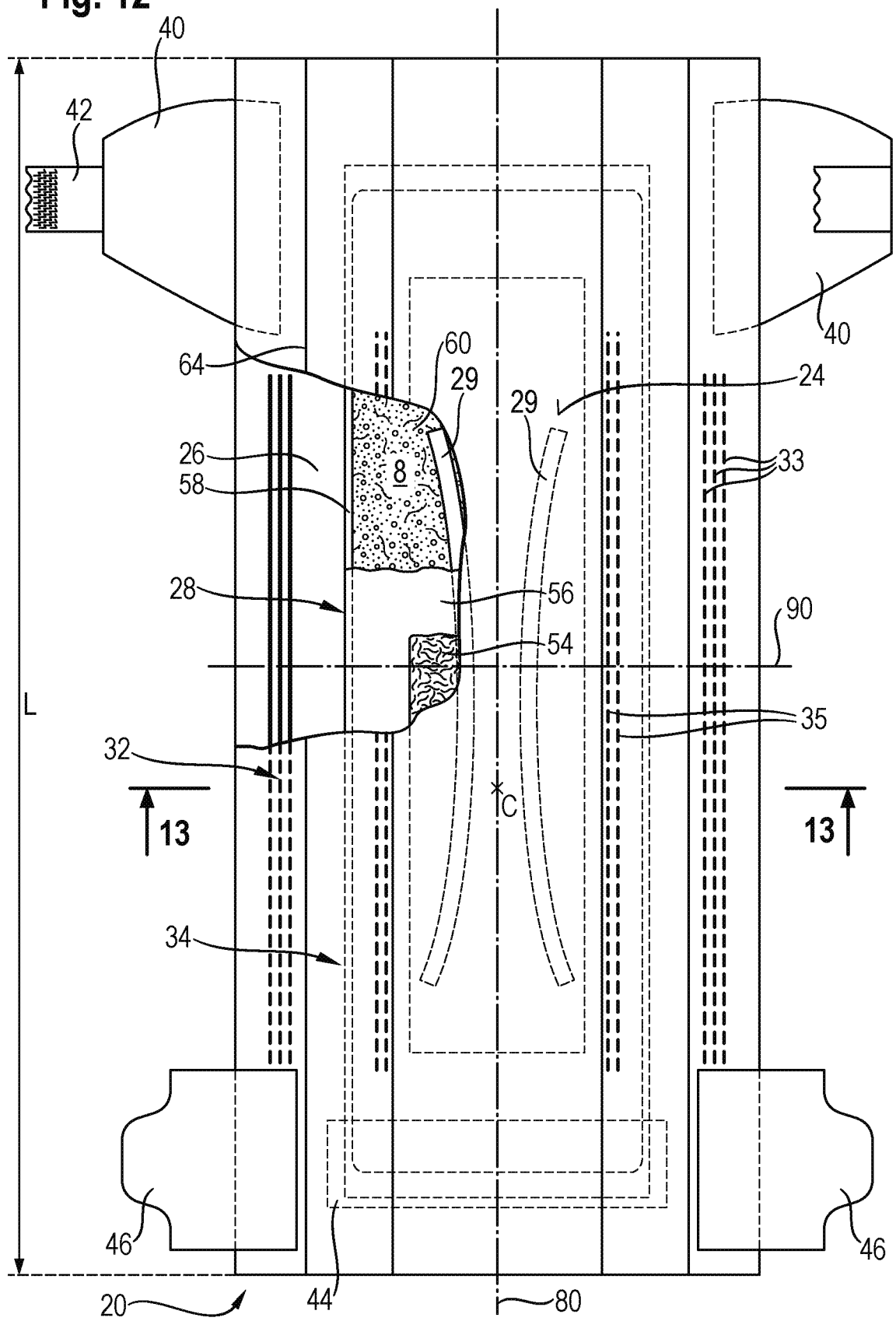
FIG. 12 is a top view of an exemplary absorbent article in the form of a diaper which may comprise the topsheet of the present disclosure, with area(s) substantially free of absorbent material.
Figure 13:
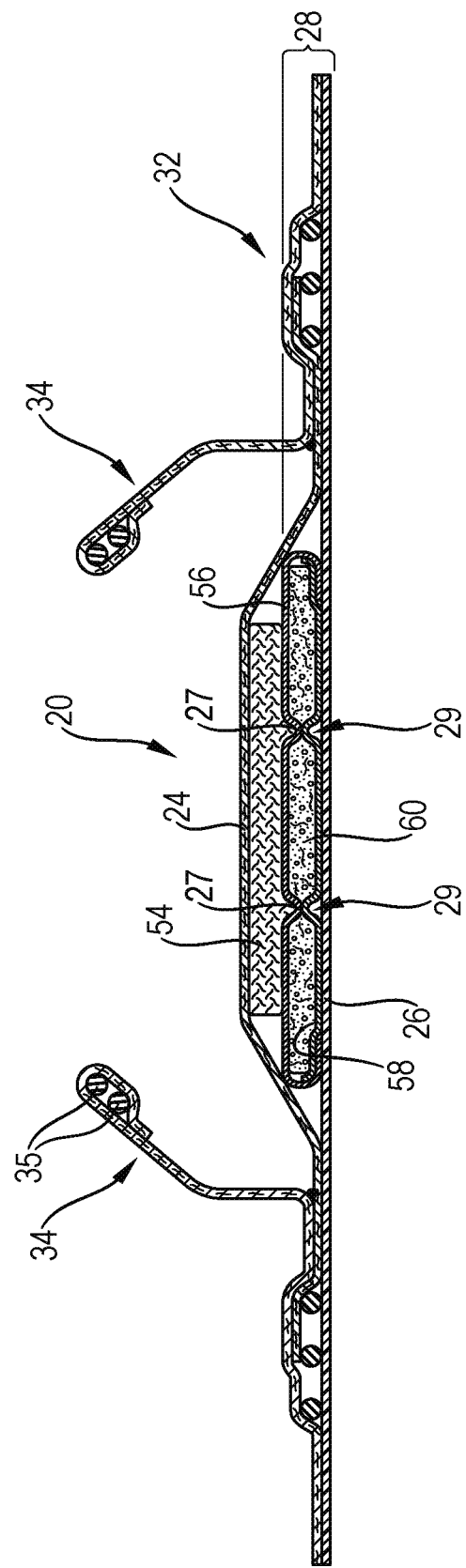
FIG. 13 is a transversal cross-section of the article of FIG. 12.
Figure 14:
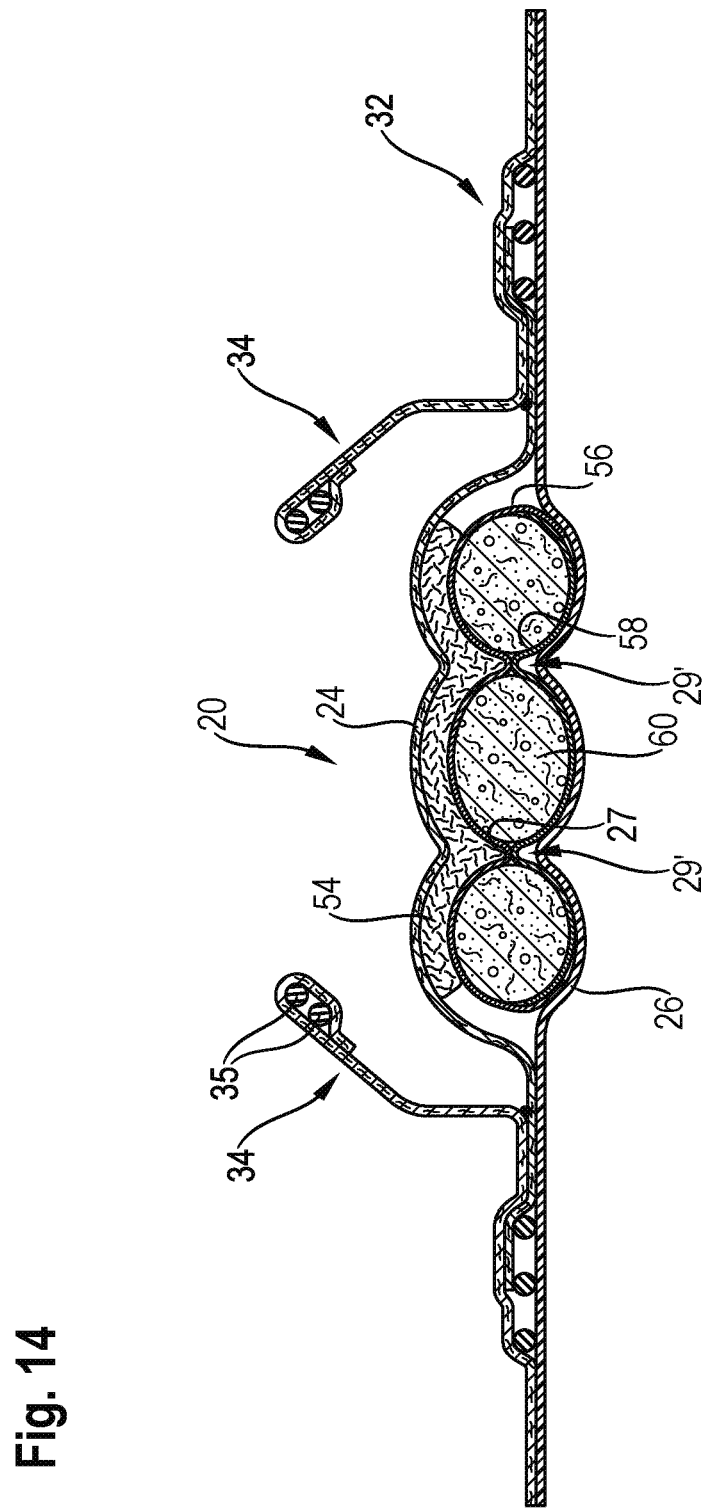
FIG. 14 is a transversal cross-section of the article taken at the same point as FIG. 13 where channels hare formed in the core as a result of the diaper being loaded with fluid.

As shown in FIGS. 10 and 11, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as superabsorbent polymer particles 66 and/or cellulose fibers, as well as other absorbent and non-absorbent materials commonly used in absorbent articles (e.g. thermoplastic adhesives immobilizing the superabsorbent polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent core may comprise one or more substrate layer(s) (such as nonwoven webs or paper tissue), superabsorbent polymer particles disposed on the one or more substrate layers, and a thermoplastic composition typically disposed on the superabsorbent polymer particles. Typically, the thermoplastic composition is a thermoplastic adhesive material. In one embodiment, the thermoplastic adhesive material forms a fibrous layer which is at least partially in contact with the superabsorbent polymer particles on the one or more substrate layers and partially in contact with the one or more substrate layers. Auxiliary adhesive might be deposited on the one or more substrate layers before application of the superabsorbent polymer particles for enhancing adhesion of the superabsorbent polymer particles and/or of the thermoplastic adhesive material to the respective substrate layer(s). The absorbent core may also include one or more cover layer(s) such that the superabsorbent polymer particles are comprised between the one or more substrate layer(s) and the one or more cover layer(s). The one or more substrate layer(s) and the cover layer(s) may comprise or consist of a nonwoven web. The absorbent core may further comprise odor control compounds.

The absorbent core may consist essentially of the one or more substrate layer(s), the superabsorbent polymer particles, the thermoplastic composition, optionally the auxiliary adhesive, optionally the cover layer(s), and optionally odor control compounds.

The absorbent core may also comprise a mixture of superabsorbent polymer particles and airfelt, which may be enwrapped within one or more substrate layers, such as nonwoven webs or paper tissue. Such absorbent cores may comprise from 30% to 95%, or from 50% to 95% of superabsorbent polymer particles by weight of the absorbent material and may comprise from 5% to 70%, or from 5% to 50% of airfelt by weight of the absorbent material (for these percentages, any enwrapping substrate layers are not considered as absorbent material). The absorbent core may also be free of airfelt and may comprise 100% of superabsorbent polymer particles by weight of the absorbent material.

The absorbent articles of the present disclosure, especially diapers and pants, may comprise an acquisition layer 52, a distribution layer 54, or combination of both (all herein collectively referred to as acquisition-distribution system "ADS" 50).

A hydrophilic hot melt adhesive may be used to bond the topsheet to the acquisition layer and/or the distribution layer and/or the absorbent core. This may help to reduce the run-off.

The function of the ADS 50 is typically to quickly acquire the fluid and distribute it to the absorbent core in an efficient manner. The ADS may comprise one, two or more layers.

The ADS may be free of superabsorbent polymer. The prior art discloses many types of acquisition-distribution systems, see for example WO2000/59430, WO95/10996, U.S. Pat. No. 5,700,254, WO02/067809. However, the superabsorbent polymer particles may also be comprised by the ADS.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 g/m$^2$, in particular from 80 to 300 g/m$^2$.

The distribution layer may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example, a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13 to 15 g/m$^2$ high wet strength made of cellulose fibers from supplier Havix.

The diaper may also comprise elasticized gasketing cuffs 32 and barrier leg cuffs 34, which provide improved containment of liquids and other body exudates especially in the area of the leg openings. Usually each gasketing cuffs 32 and barrier cuffs 34 will comprise one or more elastic string 33 and 35, represented in exaggerated form on FIGS. 10 and 11. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 10 and 11 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

The topsheet 24 of the present disclosure may comprise a first layer and a second layer. The second layer of the topsheet may comprise longitudinal edges and lateral edges. The longitudinal edges of the second layer may be parallel to the longitudinal centerline 80 of the diaper 20.

The width of the second layer of the topsheet 24 in a direction parallel to the transversal centerline 90 may be higher than the width of the first layer of the topsheet 24. The longitudinal edges of the second layer may be bonded to the gasketing cuffs of the absorbent article.

As the first layer of the topsheet 24 comprises at least 15% by weight of natural fibers by total weight of the first layer, the first layer cannot be bonded to the gasketing cuffs of the absorbent article via known bonding methods such as heat and pressure. Glue can be an alternative to bond the first layer of the topsheet 24 to the gasketing cuffs. However, there is not a good interaction between the glue and the lotions applied on the skin of the wearer of the absorbent article. Therefore, having a topsheet 24 with a second layer that has a width higher than the width of the first layer of the topsheet 24 enables to bond the longitudinal edges of the second layer of the topsheet 24 to the gasketing cuffs via any known bonding methods such as heat and pressure.

The acquisition layer 52 of the diaper may receive the body fluid exudates from the topsheet 24 and can directly transmit the body fluid exudates to the optional distribution layer 54. Leakage can thus be reduced.

Test Methods:
Tensile Strength Test Method:
The Tensile Strength Method is used to determine the Tensile Strength of topsheet material, or of the first and/or second layer of the topsheet.

If a topsheet, or a layer of the topsheet layer (depending what is to be measured) is available in its raw material form, a specimen 50 mm±0.5 mm in length and 50 mm±0.5 wide is cut from the raw material with the 50 mm dimension oriented in the CD direction when CD strength is measured, or oriented in the MD direction when MD strength is measured. Otherwise, a topsheet specimen/topsheet layer specimen 50 mm±0.5 in length and 50 mm±0.5 wide is removed from the absorbent article, centered at the intersection of the longitudinal and lateral centerlines of the absorbent article, with the 50 mm wide dimension being oriented along the lateral width of the absorbent article. For the purpose of removing the topsheet/topsheet layer from the absorbent article, a razor blade is used to excise the topsheet from the underling layers of the absorbent article around the outer perimeter of the 50 mm±0.5×50 mm±0.5 area. A cryogenic spray (such as Cyto-Freeze, Control Company, Houston Tex.) can be used to remove the topsheet specimen from the underling layers, if necessary four more specimens are prepared in a similar manner. The first layer specimen of the topsheet can be removed from the second layer specimen of the topsheet in a similar manner as the topsheet specimen is removed from the underlying layers.

If the dimension of the absorbent article does not allow for a topsheet specimen/topsheet layer specimen with 50 mm±0.5 wide then a 25±0.5 mm wide specimen is removed from the absorbent article, centered at the intersection of the longitudinal and lateral centerlines of the absorbent article, with the 25 mm wide dimension being oriented along the lateral width of the absorbent article. For the purpose of removing the topsheet from the absorbent article, a razor blade is used to excise the topsheet from the underling layers of the absorbent article around the outer perimeter of the 25±0.5 mm×50±0.5 mm area. A cryogenic spray (such as Cyto-Freeze, Control Company, Houston Tex.) can be used to remove the topsheet specimen from the underling layers, if necessary five more specimens are prepared in a similar manner. The first layer specimen of the topsheet can be removed from the second layer specimen of the topsheet in a similar manner as the topsheet specimen is removed from the underlying layers.

The topsheet specimens/topsheet layer specimens are analyzed according to the INDA/EDANA WSP 110.4(09), with the following specific choices and modifications: sample preload is 0.0 N; crosshead speed during test is 100 mm/min; specimen option A is used with width is 50 mm (corresponding to the CD or lateral-axis dimension of each specimen when CD strength is measured, or corresponding to the MD dimension when MD strength is measured); in case specimen is 25 mm wide then specimen option B is used; a constant rate of extension (CRE) is used; gauge length is 50±0.5 mm.

The breaking force for each specimen are recorded in units of force per width (N/5 cm). The CD strength or MD strength (corresponding to the tested direction), defined as the arithmetic mean of the breaking force among the 5+1 specimens, is calculated and reported to the nearest 0.1 N/(5 cm).

Delamination Force Test Method:
The Delamination Force Method is used to determine the Delamination Force a laminated topsheet material.

A topsheet specimen 150.0±0.1 mm in length and 50.8±0.1 mm wide is removed from the absorbent article, centered at the intersection of the longitudinal and lateral centerlines of the absorbent article, with the 50.8 mm wide dimension being oriented along the lateral width of the absorbent article. For the purpose of removing the topsheet from the absorbent article, a razor blade is used to excise the topsheet from the underling layers of the absorbent article around the outer perimeter of the 150.0 mm×50.8 mm area. A cryogenic spray (such as Cyto-Freeze, Control Company, Houston Tex.) can be used to remove the topsheet specimen from the underling layers, if necessary. If the dimensions of the absorbent article do not allow to excise an area of 50.8 mm×150 mm, then the largest possible rectangular topsheet area will be excised from the absorbent article with the procedure above. Prepare 4 more specimens are prepared in like fashion.

The topsheet specimens are analyzed according to the National Standard of People's Republic of China standard method GB 8808-88, with the following specific choices and modifications: Testing speed Method A is used in which the crosshead speed is 300 mm/min; the specimens used are 50.8±0.03 mm in wide and 150.0±0.1 mm long; and specimens are oriented in the tensile tester with the dimension of the specimen that was parallel to the longitudinal axis of the article being oriented parallel to the direction of crosshead travel.

The average peel force determined according to GB 8808-88 is defined as the Delamination Force and is reported to the nearest 0.01 N/(50.8 mm).

Figure 15:
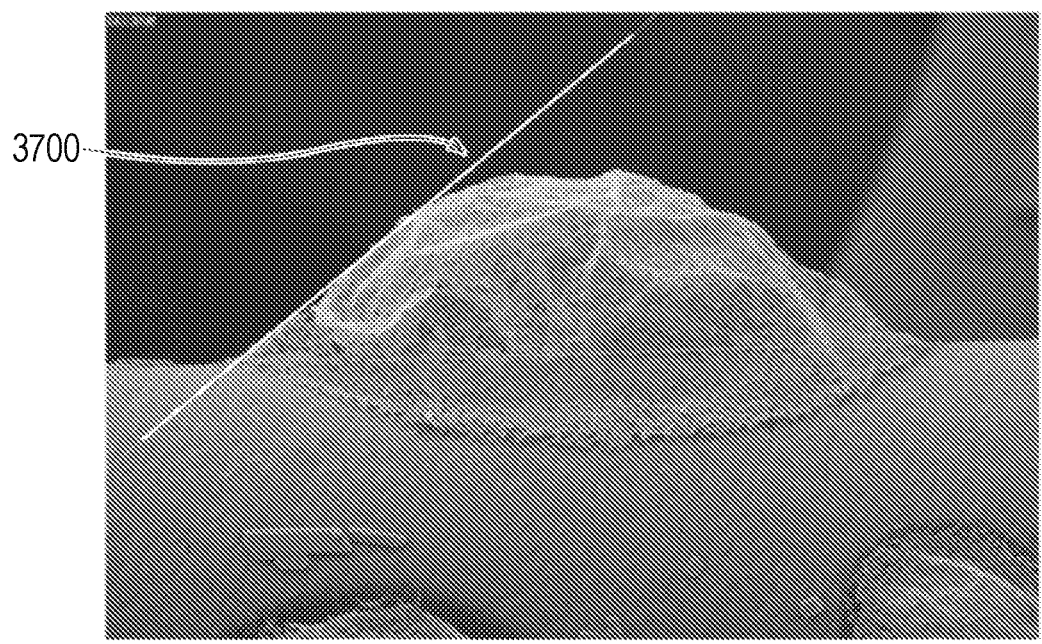
FIG. 15 is a photomicrograph depicting exemplary water droplet on fibers for the contact angle test method disclosed herein.

Contact Angle Test Method:

A rectangular specimen measuring 1 cm×2 cm is cut from the topsheet of a disposable absorbent product taking care not to touch the surface of the specimen or to disturb the structure of the material. The specimen has a length of (2 cm) aligned with a longitudinal centerline of the article. The specimen is handled gently by the edges using forceps and is mounted flat with the skin-facing side up on an SEM specimen holder using double-sided tape. The specimen is sprayed with a fine mist of water droplets generated using a small hobby air-brush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the image taken as is shown via lines 3700 in FIG. 15.

Such method is performed on the land region of the first surface of the first layer to measure the First Surface Land Area Contact Angle. Ten separate droplets, located on the land area in the middle between two neighboring apertures, are imaged from which twenty contact angle measurements are performed (one on each side of each imaged droplet), and the arithmetic average of these twenty contact angle measurements is calculated and reported as the First Surface Land Area Contact Angle.

Such method is also performed on the apertures to measure the Apertures Contact Angle. Ten separate droplets, located near the top of three separate apertures, and ten droplets, located near the bottom of the same three separate apertures, are imaged from which forty contact angle measurements are performed (one on each side of each imaged droplet), and the arithmetic average of these forty contact angle measurements is calculated and reported as the Apertures Contact Angle.

Percent Effective Area, Aperture Dimension and Inter-Aperture Distance Measurement Test Method:

Effective aperture dimensions, percent effective area and inter-aperture distance measurements are obtained from aperture specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif., or equivalent). The scanner is interfaced with a computer running an image analysis program (a suitable program is ImageJ v. 1.47, National Institute of Health, USA, or equivalent). The specimen images are distance calibrated against an acquired image of a ruler certified by NIST. The aperture specimen is backed with a black glass tile (P/N 11-0050-30, available from HunterLab, Reston, Va., or equivalent) prior to acquiring the image. The resulting grayscale image is then converted to a binary image via a threshold gray-level value, enabling the separation of open aperture regions from specimen material regions, and these regions analyzed using the image analysis program. All testing is performed in a conditioned room maintained at about 23±2° C. and about 50±2% relative humidity.

Sample Preparation:

To obtain a specimen, the absorbent article is taped to a rigid flat surface in a planar configuration. Any leg elastics present may be cut to facilitate laying the article flat. The outer boundary of the region lying above the absorbent core of the article is identified and marked on the apertured layer. The specimen of apertured layer is removed from the underlying layers of the article by cutting around the outer perimeter of the article with a razor blade. The apertured layer specimen is carefully removed such that its longitudinal and lateral extension is maintained to avoid distortion of the apertures. A cryogenic spray (such as Cyto-Freeze, Control Company, Houston Tex., or equivalent) can be used to remove the specimen from the underlying layers if necessary. Five replicate specimens obtained from five substantially similar articles are prepared for analysis. An apertured substrate raw material is prepared for testing by extending or activating it under the same process conditions, and to the same extent, as it would be for use on the absorbent article. The samples are conditioned at about 23° C.±2 C.° and about 50%±2% relative humidity for 2 hours prior to testing.

Image Acquisition:

The ruler is placed on the scanner bed such that it is oriented parallel to the sides of the scanner glass. An image of the ruler (the calibration image) is acquired in reflectance mode at a resolution of 6400 dpi (approximately 252 pixels per mm) and in 8-bit grayscale. The calibration image is saved as an uncompressed TIFF format file. After obtaining the calibration image, the ruler is removed from the scanner glass and all specimens are scanned under the same scanning conditions. An apertured specimen is placed onto the center of the scanner bed, lying flat, with the outward facing surface of the specimen facing the scanner's glass surface. The corners and edges of the specimen are secured such that its original longitudinal and lateral extension, as on the article prior to removal, is restored. The specimen is oriented such that the machine direction (MD) and cross direction (CD) of the apertured specimen layer are aligned parallel with and perpendicular to the sides of the scanner's glass surface and that the resulting specimen image has the MD vertically running from top to bottom. The black glass tile is placed on top of the specimen, the scanner lid is closed, and a scanned image of the entire specimen is acquired. The specimen image is saved as an uncompressed TIFF format file. The remaining four replicate specimens are scanned and saved in like fashion. Prior to analysis, all specimen images are cropped to the largest rectangular field of view contained within the apertured region which had been located above the absorbent core of the article.

Percent Effective Aperture Area Calculation:

The calibration image file is opened in the image analysis program and a linear distance calibration is performed using the imaged ruler. This distance calibration scale is applied to all subsequent specimen images prior to analysis. A specimen image is in the image analysis program and the distance scale is set using the distance calibration. The 8-bit grayscale image is then converted to a binary image (with "zero" or "black" corresponding to the aperture regions) in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined.

Each of the discrete aperture regions is analyzed using the image analysis program. All individual aperture areas are measured and recorded to the nearest 0.01 mm², including partial apertures along the edges of the image. Any apertures with an area less than 0.3 mm² are defined as "non-effective" and discarded. The remaining apertures, so-called "effective" aperture areas that include whole and partial apertures, are summed. This sum is then divided by the total area included in the image. This value is multiplied by 100% and reported as the effective area to the nearest 0.01%.

The remaining four specimen images are analyzed similarly. The average percent effective area values to the nearest 0.01% for the five replicate specimens are calculated and reported.

Effective Aperture Dimension Measurements:

The calibration image (containing the ruler) file is opened in the image analysis program. The resolution of the original image is resized from 6400 dpi to 640 dpi (approximately 25.2 pixels per mm) using a bicubic interpolation. A linear distance calibration is performed using the imaged ruler. This distance calibration scale is applied to all subsequent specimen images prior to analysis. One specimen image is selected and opened in the image analysis program. The resolution of the original image is resized from 6400 dpi to 640 dpi (approximately 25.2 pixels per mm) using a bicubic interpolation, and a distance scale is set according to the linear distance calibration established using the calibration image. The 8-bit grayscale image is then converted to a binary image (with "zero" or "black" corresponding to the aperture regions) in the following way: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined. Two morphological operations are then performed on the binary image. First, a closing (a dilation operation, which converts any white background pixel that is touching a black aperture region pixel into a black aperture region pixel thereby adding a layer of pixels around the periphery of the aperture region, followed by an erosion operation, which removes any black aperture region pixel that is touching a white background pixel thereby removing a layer of pixels around the periphery of the aperture region, iterations=1, pixel count=1) is performed, which removes stray fibers within an aperture hole. Second, an opening (an erosion operation followed by a dilation operation, iterations=1, pixel count=1) is performed, which removes isolated black pixels. The edges of the image are padded during the erosion step to ensure that black boundary pixels are maintained during the operation. Lastly, any remaining voids enclosed within the black aperture regions are filled.

Each of the discrete aperture regions is analyzed using the image analysis software. Any partial apertures along the edges of the image are excluded so that only whole apertures are analyzed. All of the individual aperture areas, perimeters, feret diameters (length of the apertures) along with its corresponding angle of orientation in degrees from 0 to 180, and minimum feret diameters (width of the apertures) are measured and recorded. Individual aperture areas are recorded to the nearest 0.01 mm², aperture perimeters and feret diameters (length and width), to the nearest 0.01 mm, and aperture angles to the nearest 0.01 degree. Any apertures with an area less than 0.3 mm² are discarded as "non-effective". The number of remaining "effective" apertures is recorded and divided by the area of the image. This quotient is recorded as the Aperture Density value to the nearest 0.1 apertures per cm². The angle of orientation for an aperture aligned with the MD (vertical in the image) is defined as 90 degrees. Apertures with a positive slope, increasing from left to right, have an angle between zero and 90 degrees. Apertures with a negative slope, decreasing from left to right, have an angle between 90 and 180 degrees. The angles of individual apertures are used to calculate an Absolute Aperture Angle by subtracting 90 degrees from the original angle of orientation and taking its absolute value. In addition to these measurements, the Aspect Ratio, defined for each aperture as the quotient of its length divided by its width, is recorded. This analysis is repeated for each of the remaining images of the four replicate specimens. The statistical mean and standard deviation for each of the effective aperture dimensions (area, perimeter, length, width, and angle), the Absolute Aperture Angle and the Aspect Ratio measurements are calculated and using all of the aperture values recorded from all specimens and reported. The percent relative standard deviation (RSD) for each of the effective aperture dimensions, the Absolute Aperture Angle and the Aspect Ratio measurements is calculated and reported by dividing the standard deviation by the mean and multiplying by 100%.

Inter-Aperture Distance Measurements:

The mean, standard deviation, median, and maximum distance between the apertures are measured by further analyzing the binary images for each specimen that were analyzed for the aperture dimension measurements. For each image, a Voronoi operation is performed on a resized, spatially calibrated, binary image (described above). The Voronoi operation generates an image in which regions or "cells" bounded by lines of pixels having equal distance to the borders of the two nearest pattern apertures in which the pixel values of these boundary lines are outputs from a Euclidian distance map (EDM) of the binary image and in which all other pixel values are zero. (An EDM is a transformed image in which each inter-aperture pixel in the binary image is replaced with a value equal to that pixel's distance from the nearest pattern aperture.) Statistical analysis of the nonzero distance values (that is, the Euclidean distance values along the boundary lines) present in the Voronoi-transformed image is performed. The resulting mean, standard deviation, median and maximum inter-aperture distances for the image are calculated and then multiplied by a factor of two to reflect full distance between aperture features. These statistical metrics are reported to the nearest 0.01 mm. This procedure is repeated for all specimen images. The percent relative standard deviation (RSD) for the inter-aperture distance by dividing the standard deviation by the mean and multiplying by 100%.

Post-Conditioning Contact Angle Test Method:

A topsheet specimen is removed from an absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of a 10±1 cm×10±1 cm area. If the topsheet is of insufficient size to permit a 10±1 cm×10±1 cm area to be excised from the intersection of the longitudinal and lateral centerlines, the largest square of topsheet that can be extracted is excised and used as the topsheet specimen henceforth. The specimen is carefully removed such that its longitudinal and lateral extension are maintained. A cryogenic spray (such as Cyto-Freeze, Control Company, Houston Tex.) can be used to remove the topsheet specimen from the underling layers, if necessary.

A solution (the "conditioning solution") is prepared with 0.9% (w/w) NaCl and 0.3% (w/w) Na-cholate by using distilled water, NaCl with purity higher than 99% and NA-cholate with purity higher than 96%. The conditioning solution is heated to 40±2° C. and is held as this temperature for the entirety of this sample preparation. 100 (+/−10) ml of the temperature-maintained conditioning solution is filled into a glass container with a diameter of 150 to 180 mm. The test specimen is put into the glass container with the conditioning solution by keeping the specimen beneath the surface of the solution, and the glass container is placed into a climate chamber at 40 (+/−2) ° C. for 30±2 minutes.

The test specimen is then taken out of the solution by using clean metal tweezers and placed on blotting paper (larger than the test specimen). Once the blotting paper is partly wetted, new blotting paper is used. This is repeated until no further wetness is transferred to the blotting paper. The specimen is then transferred to a dry clean glass container with a diameter of 150 to 180 mm, and the glass container is placed into a climate chamber at 40 (+/−2) ° C. for 30 (+/−2) minutes. The specimen is then let cool down to room temperature. A rectangular specimen, measuring 1 cm×2 cm, is cut from the conditioned test specimen, according to the Contact Angle Method. The First Surface Land Area contact angle of the specimen after conditioning, measured according to the Contact Angle Method, is reported as the First Surface Land Area Post-Conditioning Contact Angle.

Run-Off Test Method:

Run-off is measured according to basic method for testing hydrophilic nonwovens in WSP 80.9 (05), standard test method for nonwoven run-off. The inclination angle is set to be 25°+/−1°. A total mass of test liquid of 25±0.5 g is used.

The topsheet sample is removed from the absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of the 100 mm×280 mm area. The specimen is carefully removed such that its longitudinal and lateral extension are maintained. A cryogenic spray (such as Cyto-Freeze, Control Company, Houston Tex.) can be used to remove the topsheet specimen from the underling layers, if necessary. The topsheet layer with 100 mm width is centered over the two 140 mm wide layers of reference filter paper.

If the dimensions of the absorbent article do not allow to excise an area of 100 mm×280 mm, then the largest possible rectangular topsheet area will be excised from the absorbent article with the procedure above. Multiple specimens will be removed from multiple absorbent articles and will be connected to each other with a 5 mm wide overlap on each neighboring side between two separate pieces. A double tape adhesive will be placed in the 5 mm wide overlap area, between the two layers being stitched together. This procedure will allow to create a 100 mm×280 mm area to be used according to basic method for testing hydrophilic nonwovens in WSP 80.9 procedure. For the testing, the tube, supplying the test liquid, will be placed between any overlap areas, in machine direction or cross direction.

Storage Modulus (G') Test Method:

Dynamic Mechanical Analysis (DMA) to Determine G' for Thermoplastic Compositions—Temperature Sweep—Principle A dynamic mechanical analysis (DMA) is done. An oscillatory shear stress is continuously applied to the composition resulting in an oscillatory strain at constant amplitude, which is small enough to ensure fully recoverable deformation, whereas the temperature is decreased in discrete steps. The relationship between the sinusoidal stress applied and the resulting strain response as well as the shift between both measures on the time axis are measured. The results are quantified by Storage Modulus [G'], Loss Modulus [G"] and Loss Factor [tan δ] of the composition in dependence of temperature.

Instrument: TA Instruments AR G2

Procedure:

1. Use a rheometer with 8 mm plate/plate geometry consisting of an upper steel plate (diameter: 8 mm) and a lower peltier or heating plate enabling temperature control. The rheometer needs to be capable of applying temperatures from 0° C. to 220° C.
2. Calibrate Rheometer according to instrument manual.
3. Cut off and weigh a piece of composition of 0.37 g+/−0.01 g and place it onto the center of the Peltier or heating plate of the rheometer and set the temperature to 160° C.
4. After the composition is molten, slowly lower the upper plate to the geometry gap of 1000 micrometer. The velocity of the rheometer head must not exceed 1000 micrometer per second in order to achieve good contact between the composition and the upper plate without damaging the composition sample.
5. Cover the geometry with the geometry cover for 2 minutes so that the upper plate can heat up and the composition gets completely molten.
6. Remove the cover and rotate the upper plate manually to distribute the composition evenly between the upper plate and the Peltier or heating plate and to ensure full contact of the composition to the upper plate.
7. Afterwards cover the geometry with the geometry cover for another 2 minutes.
8. Remove the geometry cover and check whether the composition is distributed evenly.
9. Set Axial force control to 0.2 N with a sensitivity+/−0.1 N Start Temperature Sweep from 160° to 0° C. with a temperature ramp of 3° C. per minute.

Strain Amplitude: 0.05%

Angular frequency: 6.28319 rad/s

Calculation/Reporting:

From the temperature sweep report the following parameters:

Glass transition temperature in ° C. (The glass transition temperature is defined at the peak maximum of the tan δ value)

Cross-over temperature in ° C. (The cross-over-temperature is found at the end of the rubber-plateau towards higher temperatures indicating the beginning of the terminal zone. At the cross-over-temperature storage- and loss modulus equal and tan δ value is 1)

Storage modulus at from 0° C. to 160° C. with 5° C. increments (e.g. 0° C., 5° C., 10° C. and so on) in Pascal.

Martindale Abrasion Resistance Test Method:

The Martindale Abrasion Resistance Test Method is used to determine the abrasion resistance of the of topsheet material.

If a topsheet is available in its raw material form, a specimen with 140 mm±0.5 mm diameter is cut from the raw material. Otherwise, a topsheet specimen with 140 mm±0.5 mm diameter is removed from the absorbent article, centered at the intersection of the longitudinal and lateral centerlines of the absorbent article. For the purpose of removing the topsheet from the absorbent article, a razor blade is used to excise the topsheet from the underling layers of the absorbent article around the outer perimeter of the area with 140 mm±0.5 mm diameter. A cryogenic spray (such as Cyto-Freeze, Control Company, Houston Tex.) can be used to remove the topsheet specimen from the underling layers, if necessary 4 more specimens are prepared in like fashion.

The topsheet specimens are analyzed according to the INDA/EDANA WSP 20.5 (05) with Lissajous figure trajectory and with the following specific choices and modifications: The required weight is added to give the desired pressure of 2.9 kPa for each specimen. The Martindale equipment is set for 25 cycles/minute. The standard abradant material has a surface hardness of 56 A Durometer. The Shore A is 56±1. The thickness of the abradant material is 1.05±0.1 mm.

If the topsheet is not apertured, the test ends when a hole that is larger than 5 mm in any direction appears on two of the four specimens. If no holes appear, the test is terminated at 480 cycles. The test is run by stopping every 20 cycles and specimens are investigated to assess whether criteria is met. The cycles number is recorded and reported as the Abrasion Integrity Parameter.

If the topsheet is apertured then the test ends when a hole that is 5 mm larger (in any direction) than the largest aperture dimension appears on two of the four specimens. If no holes appear, the test is terminated at 480 cycles. The test is run by stopping every 20 cycles and specimens are investigated to assess whether criteria is met. The cycles number is recorded and reported as the Abrasion Integrity Parameter.

EXAMPLES

The following are non-limiting examples of the topsheet of the present disclosure and of comparative examples. The examples are given solely for the purpose of illustration and are not to be construed as limitations of the present disclosure, as many variations thereof are possible without departing from the spirit and scope of the present disclosure, which would be recognized by one of ordinary skill in the art.

CD Strength and MD Strength: Examples 1 to 5:

Preparation of the Samples:

For each sample, the two layers forming the topsheet are detached according to the tensile strength test method. The first layer that is in contact with the skin of the wearer of the absorbent article when the topsheet is used in an absorbent article is presented below. For every example, the hydrophobic surfactant is the same.

Example 1 is a 100% cotton spunlace nonwoven web that was produced with conventional uni-lapper process as known in the art. The nonwoven web of example 1 becomes hydrophobic by applying a hydrophobic surfactant to the nonwoven web via a dipping process.

Example 2 is a 100% cotton spunlace nonwoven web that was produced with cross-lapper process as described above. The nonwoven web of example 2 becomes hydrophobic by applying the hydrophobic surfactant to the nonwoven web via a dipping process.

Examples 3 and 4 are similar spunlace nonwoven web than the nonwoven web from example 2.

Example 3 comprises a partial hydrophobic application of the hydrophobic surfactant. That is to say that only 1 side of the nonwoven web comprises a hydrophobic surfactant. Therefore, one side of the nonwoven web of example 3 is hydrophilic and the other side of the nonwoven web of example 3 is hydrophobic.

Example 4 is a hydrophilic spunlace nonwoven web without any hydrophobic application.

Example 5 is a 100% cotton spunlace nonwoven web that was produced with a cross-lapper process. The nonwoven web of example 5 is pre-apertured. Indeed, apertures have been creating in the nonwoven web by using 8 mesh belt (8 holes/inch$^2$) during a hydroentanglement process. The nonwoven pre-apertured web of example 5 becomes hydrophobic by applying the hydrophobic surfactant to the nonwoven web via a dipping process.

Example 1 is a comparative example. Examples 2 to 5 are examples according to the present disclosure.

All the nonwoven webs from the examples were deformed by a three-dimensional embossing process (3D embossing process) and were apertured by an apertured process as described above (see FIGS. 5 to 8).

Figure 16:
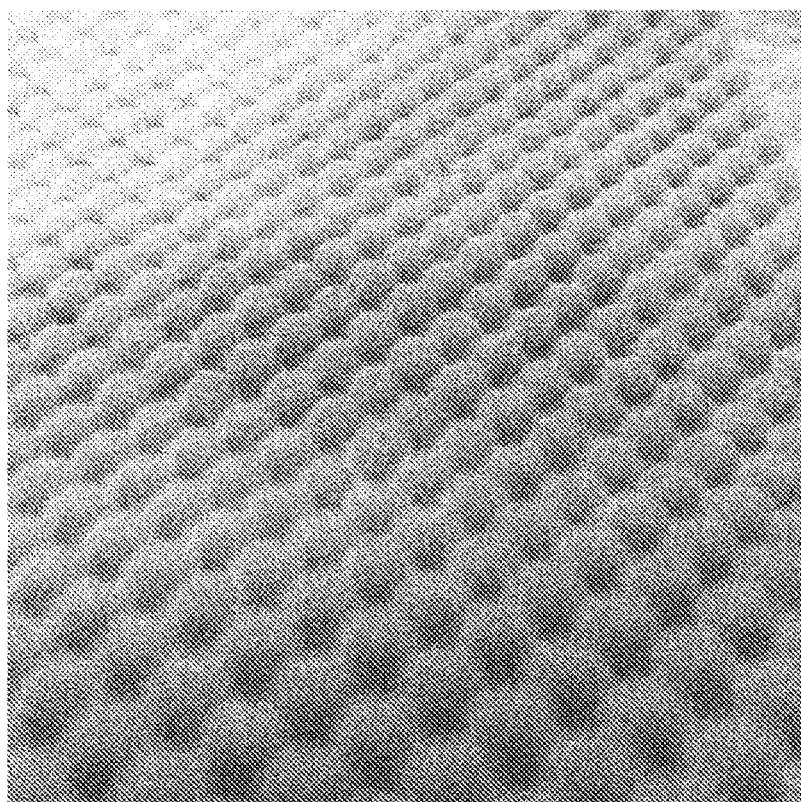
FIG. 16 is a photograph of a nonwoven material used as a topsheet having protrusions and apertures.

The picture of the three-dimensional pattern used for every example is shown in FIG. 16.

Results:

The Table below provides the mechanical strength in CD (Cross direction) before and after the nonwoven webs are textured and apertured to form a three-dimensional, apertured webs.

The CD (Cross direction) strength are measured according to the tensile strength test method disclosed herein.

|  | Basis weight (in g/m$^2$) | CD strength (in N/(5 cm)) | | MD Strength (in N/(5 cm)) | |
|---|---|---|---|---|---|
|  |  | Before 3D embossing/ aperturing process | After 3D embossing/ aperturing process | Before 3D embossing/ aperturing process | After 3D embossing/ aperturing process |
| Example 1 (comparative) | 30 | 3.3 | 1.6 | 17.9 | 8.9 |
| Example 2 | 35 | 17.6 | 4.1 | 17.9 | 6.6 |
| Example 3 | 35 | 22.4 | 5.3 | 27.3 | 5.9 |

-continued

| | Basis weight (in g/m$^2$) | CD strength (in N/(5 cm)) | | MD Strength (in N/(5 cm)) | |
|---|---|---|---|---|---|
| | | Before 3D embossing/ aperturing process | After 3D embossing/ aperturing process | Before 3D embossing/ aperturing process | After 3D embossing/ aperturing process |
| Example 4 | 35 | 24.5 | 5.5 | 33.6 | 9.1 |
| Example 5 | 45 | 36.9 | 22.0 | 27.3 | 13.7 |

For example 1, the nonwoven webs produced with this conventional process, i.e. conventional uni-lapper process, has a minimum CD strength of less than 3N/(5 cm) after being textured and apertured. The structural and mechanical strength of the three-dimensional textured/apertured nonwoven web of example 1 is reduced.

For example 2, the cross-lapped nonwoven web from example 2 has a higher CD strength than example 1. The CD strength of the three-dimensional textured/apertured nonwoven web from example 2 is more than 3N/(5 cm).

The three-dimensional textured/apertured nonwoven web from example 2 has a higher mechanical strength than the three-dimensional textured/apertured nonwoven web of example 1.

The three-dimensional textured/apertured nonwoven web from examples 3 and 4 have a higher mechanical strength than the three-dimensional textured/apertured nonwoven web of example 2. It demonstrates that hydrophobic treatment applied on the nonwoven webs may reduce the mechanical strength of the nonwoven webs even before the three-dimensional texturing and aperturing processes.

Concerning example 5, we can see that when the nonwoven web is pre-apertured before being subjected to the three-dimensional texturing and aperturing processes, the three-dimensional textured/apertured nonwoven web can retain a major part of its initial strength.

The three-dimensional textured/apertured nonwoven web from example 5 has a higher mechanical strength than the three-dimensional textured/apertured nonwoven web of example 1.

Delamination Force: Examples 6 to 8:
Preparation of the Samples:

Examples 6, 7 and 8 are topsheets comprising a first layer and a second layer. The first layer is a 100% cotton spunlace nonwoven web that was produced with cross-lapper process as described above. The basis weight of the first layer is 35 g/m$^2$. This first layer is a hydrophilic spunlace nonwoven web without any hydrophobic application. The second layer of the topsheet of example 1 is an air-through carded nonwoven web that comprises 4 denier of bicomponent PE/PET fibers. The basis weight of the second layer is 25 g/m$^2$.

In each example, the first layer is attached to the second layer in bonding areas by a hot melt adhesive.

The quantity of hot melt adhesive applied on the bonding areas may vary for each example.

Figure 17:
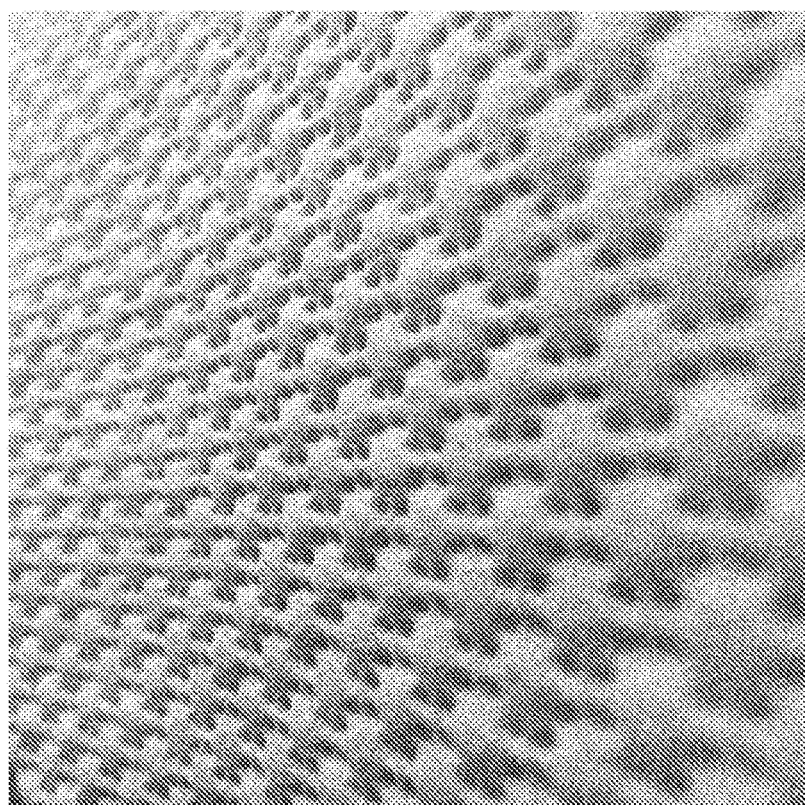
FIG. 17 is a photograph of a nonwoven material used as a topsheet having protrusions and apertures.

All the nonwoven webs from the examples were deformed by a three-dimensional embossing process and were apertured by an apertured process as described above (see FIGS. 5 to 8). The picture of the three-dimensional pattern used for every example is shown in FIG. 17.

Examples 6 to 8 are examples according to the present disclosure.
Result:

The delamination force between the first layer and the second layer of the topsheet of each sample is measured according to the delamination force test method disclosed herein.

| | Hot melt basis weight (in g/m$^2$) | Delamination force (in N/(2 inch)) |
|---|---|---|
| Example 6 | 1 | 0.41 |
| Example 7 | 2 | 0.60 |
| Example 8 | 4 | 2.34 |

The delamination force between the first layer and the second layer of the topsheet for examples 6 to 8 is higher than 0.25 N/(50.8 mm). Therefore, the topsheets of examples 6 to 8 keep their integrity during in-use conditions. When the topsheets of examples 6 to 8 are used in an absorbent article, the first layer and the second layer of the topsheets are not detached by the move of the wearer of the absorbent article.

Abrasion Integrity: Examples A to D:

Examples A, B, C and D are topsheet material with a first layer and a second layer. The first layers correspond to Example materials 1, 2, 3 and 4 above. Example A is a comparative Example. The second layer of the topsheets is an air-through carded nonwoven web that comprises 4 denier of bicomponent PE/PET fibers. The basis weight of the second layer is 25 g/m$^2$. In each example, the first layer is attached to the second layer in bonding areas by a hot melt adhesive. The quantity of hot melt adhesive applied on the bonding areas may vary for each example.

All the nonwoven webs from the examples were deformed by a three-dimensional embossing process and were apertured by an apertured process as described above (see FIGS. 5 to 8). The picture of the three-dimensional pattern used for every example is shown in FIG. 17.

| | Basis Weight [g/m$^2$] | Abrasion Integrity Parameter [Cycles] |
|---|---|---|
| Comparative Example A (with first layer of comparative Example 1) | 30 | 40 |
| Example B (with first layer of Example 2) | 35 | 200 |
| Example C (with first layer of Example 3) | 35 | 120 |
| Example D (with first layer of Example 4) | 35 | 320 |

Inventive examples B to D exhibit a significant higher Abrasion Resistance versus comparative example A.
Examples of Commercially Available Cotton Fibers:

Following table shows results of two different cotton type with equipment USTER® AFIS PRO:

| Sample information | L(w) (mm) | L(w) CV % | SFC(w) % < 12.7 mm | UQL(w) (mm) | L(n) (mm) | L(n) CV % | SFC(n) % < 12.7 mm | 5% L(n) (mm) |
|---|---|---|---|---|---|---|---|---|
| Marusan Bleached Organic Cotton Fibers (average of 5 lot) | 14.3 | 54.7 | 46.3 | 19.1 | 10.1 | 65.0 | 70.4 | 23.6 |
| Marusan Bleached Cotton Fibers (average of 5 lot) | 22.7 | 36.3 | 9.9 | 28.1 | 18.4 | 48.6 | 25.9 | 32.6 |

AFIS Parameter Definitions:

L(n): The mean length by number is the average fiber length of all the cotton fibers in the sample.

L(n) CV %: The variation of the fiber length around the average is ex-pressed as length variation by number or CV %.

L(n) 5%: The 5% length by number is the length of the longer 5% of all fibers in a cotton samples.

SFC(n): The short fiber content by number is the percent of all fibers in a cotton sample that are shorter than 12.7 mm.

L(w): The mean length by weight is the average fiber length of all the cotton fibers in the sample.

L(w) CV %: The variation of the fiber length around the average is ex-pressed as length variation by weight or CV %.

UQL(w): The Upper Quartile Length by weight is the length of the longer 25% of all fibers in a cotton samples.

SFC(w): The short fiber content by weight is the percent of all fibers in a cotton sample that are shorter than 12.7 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of the present disclosure.

What is claimed is:

1. A topsheet for an absorbent article, the topsheet comprising a first layer and a second layer;
   wherein the first layer is a spunlace nonwoven layer and comprises at least 15% by weight of natural fibers by total weight of the first layer;
   wherein the first layer comprises a plurality of protrusions and a plurality of apertures;
   wherein at least some of the protrusions are hollow and comprise an inside void volume between the first and second layer;
   wherein a majority of the apertures are located between the protrusions;
   wherein the plurality of protrusions and the plurality of apertures impart a three-dimensional shape to the first layer;
   wherein the first layer and the second layer are joined with each other between the plurality of the protrusions;
   wherein the second layer has a plurality of apertures at least partially aligned with the apertures of the first layer;
   wherein the first layer at least partially penetrates the second layer of the topsheet at the majority of the apertures; and
   wherein the first layer has a minimum CD strength of at least 3N/(5 cm), according to the Tensile Strength Test Method.

2. The topsheet according to claim 1, wherein the natural fibers of the first layer comprise fibers being shorter than 10 mm.

3. The topsheet according to claim 1, wherein the topsheet has an Abrasion Integrity Parameter of at least 80 cycles.

4. The topsheet according to claim 1, wherein the first layer is a cross-lapped spunlace nonwoven layer.

5. The topsheet according to claim 1, wherein the first layer comprises heat fusible fibers.

6. The topsheet according to claim 1, wherein the first layer is a nonwoven layer comprising a carrier web and a web comprising the natural fibers, with part of the web comprising the natural fibers entering the carrier web.

7. The topsheet according to claim 6, wherein the carrier web is a spunbond nonwoven or a carded nonwoven.

8. The topsheet according to claim 1, wherein the natural fibers are cotton fibers, bamboo fibers, or a mixture thereof.

9. The topsheet according to claim 1, wherein the plurality of apertures are uniformly distributed in the first layer.

10. The topsheet according to claim 1, wherein the topsheet has a Run-off of less than 40%, according to the Run-off Test Method.

11. The topsheet according to claim 1, wherein the second layer comprises synthetic fibers, natural fibers and/or combinations thereof, and wherein the synthetic fibers are single component fibers, multi-component fibers, and combinations thereof.

12. The topsheet according to claim 1, wherein the second layer is flat in areas outside of the apertures.

13. The topsheet according claim 1, wherein the second layer comprises a plurality of protrusions, wherein the plurality of protrusions impart a three-dimensional shape to the second layer, and wherein the plurality of protrusions of the first layer are at least partially aligned with the plurality of protrusions of the second layer.

14. The topsheet according to claim 1, wherein the first layer is attached to the second layer in bonding areas by a hot melt adhesive, wherein the hot melt adhesive has a storage modulus (G') higher than $0.3 \times 10^6$ Pa in the range of 0° C. and 40° C., and wherein the delamination force between the first layer and the second layer is higher than 0.25 N/(50.8 mm), according to the Delamination Force Test Method.

15. The topsheet according to claim 14, wherein the bonding areas comprise areas of the second layer which coincide with the protrusions of the first layer, and wherein the second layer has no protrusions.

16. The topsheet according to claim 1, wherein the first layer is attached to the second layer in bonding areas by embossing, and wherein the delamination force between the first layer and the second layer is higher than 0.25 N/(50.8 mm), according to the Delamination Force Test Method.

17. An absorbent article comprising:
- a longitudinal centerline;
- a transversal centerline perpendicular to the longitudinal centerline;
- the topsheet according to claim 1;
- a backsheet; and
- an absorbent core positioned intermediate the backsheet and the topsheet;
- wherein the first layer is facing towards the wearer during use of the absorbent article;
- and wherein the second layer is facing towards the absorbent core during use of the absorbent article.

18. The absorbent article according to claim 17, wherein a width of the second layer of the topsheet in a direction parallel to the transversal centerline is higher than a width of the first layer of the topsheet.

19. Then absorbent article according to claim 18, comprising gasketing cuffs, wherein the second layer comprises longitudinal edges, and wherein the longitudinal edges of the second layer are bonded to the gasketing cuffs.

20. A topsheet for an absorbent article, the topsheet comprising a first layer and a second layer;
- wherein the first layer is a spunlace nonwoven layer and comprises at least 80 by weight of cotton fibers by total weight of the first layer;
- wherein the first layer comprises a plurality of protrusions and a plurality of apertures;
- wherein a majority of the apertures are located between the protrusions;
- wherein the plurality of protrusions and the plurality of apertures impart a three-dimensional shape to the first layer;
- wherein the first layer and the second layer are joined with each other between the plurality of the protrusions;
- wherein the second layer has a plurality of apertures at least partially aligned with the apertures of the first layer;
- wherein the second layer has a first surface that faces the first layer, and wherein the first surface comprises a flat land area that is aligned with the protrusions in the first layer;
- wherein the first layer at least partially penetrates the second layer of the topsheet at the majority of the apertures; and
- wherein the first layer has a minimum CD strength of at least 3N/(5 cm), according to the Tensile Strength Test Method.

\* \* \* \* \*